United States Patent
Ledbetter et al.

(10) Patent No.: US 9,140,657 B2
(45) Date of Patent: Sep. 22, 2015

(54) DETECTION OF J-COUPLING USING ATOMIC MAGNETOMETER

(75) Inventors: Micah P. Ledbetter, Oakland, CA (US); Charles W. Crawford, Albuquerque, NM (US); David E. Wemmer, Berkeley, CA (US); Alexander Pines, Berkeley, CA (US); Svenja Knappe, Boulder, CO (US); John Kitching, Boulder, CO (US); Dmitry Budker, El Cerrito, CA (US)

(73) Assignees: The Regents of the University of California, Oakland, CA (US); The United States of America, as represented by the Secretary of Commerce, the National Institute of Standards and Technology, Washington, DC (US)

( * ) Notice: Subject to any disclaimer, the term of this patent is extended or adjusted under 35 U.S.C. 154(b) by 962 days.

(21) Appl. No.: 13/264,376

(22) PCT Filed: Apr. 13, 2010

(86) PCT No.: PCT/US2010/030897
§ 371 (c)(1),
(2), (4) Date: Mar. 30, 2012

(87) PCT Pub. No.: WO2010/120783
PCT Pub. Date: Oct. 21, 2010

(65) Prior Publication Data
US 2012/0176130 A1 Jul. 12, 2012

Related U.S. Application Data

(60) Provisional application No. 61/168,795, filed on Apr. 13, 2009.

(51) Int. Cl.
*G01V 3/00* (2006.01)
*G01N 24/08* (2006.01)
(Continued)

(52) U.S. Cl.
CPC ............. *G01N 24/08* (2013.01); *G01N 24/087* (2013.01); *G01R 33/26* (2013.01); *G01R 33/46* (2013.01); *G01R 33/445* (2013.01); *G01R 33/4608* (2013.01); *G01R 33/5605* (2013.01)

(58) Field of Classification Search
CPC ....................................... G01R 33/26
USPC .......................... 324/307, 305, 301, 300, 304
See application file for complete search history.

(56) References Cited

U.S. PATENT DOCUMENTS 6,885,192 B2 * 4/2005 Clarke et al. .................. 324/300
7,187,169 B2 * 3/2007 Clarke et al. .................. 324/307
(Continued)

OTHER PUBLICATIONS

M.P. Ledbetter, C.W. Crawford, A. Pines, D.E. Wemmer, S. Knappe, J. Kitching, D. Budker, Optical detection of NMR J-spectra at zero magnetic field, Journal of Magnetic Resonance, vol. 199, Issue 1, Jul. 2009, pp. 25-29.
(Continued)

*Primary Examiner* — Louis Arana
(74) *Attorney, Agent, or Firm* — Lawrence Berkeley National Laboratory

(57) ABSTRACT

An embodiment of a method of detecting a J-coupling includes providing a polarized analyte adjacent to a vapor cell of an atomic magnetometer; and measuring one or more J-coupling parameters using the atomic magnetometer. According to an embodiment, measuring the one or more J-coupling parameters includes detecting a magnetic field created by the polarized analyte as the magnetic field evolves under a J-coupling interaction.

11 Claims, 12 Drawing Sheets

(51) Int. Cl.
    *G01R 33/26*     (2006.01)
    *G01R 33/46*     (2006.01)
    *G01R 33/44*     (2006.01)
    *G01R 33/56*     (2006.01)

(56) References Cited

U.S. PATENT DOCUMENTS

| 8,222,899 B2* | 7/2012 | Horng et al. ............ 324/307 |
| 2007/0205767 A1 | 9/2007 | Xu et al. |

OTHER PUBLICATIONS

E.L. Hahn, D.E. Maxwell, Chemical shift and field independent frequency modulation of the spin echo envelope, Phys. Rev. 84 (1952) 1246-1247.

H.S. Gutowsky, D.W. McCall, C.P. Slichter, Nuclear magnetic resonance multiplets in liquids, J. Chem. Phys. 21 (1953) 279-292.

S. Appelt, H. Kühn, F.W. Häsing, B. Blümich, Chemical analysis by ultrahighresolution nuclear magnetic resonance in the Earth's magnetic field, Nat. Phys. 2 (2006) 105-109.

J.N. Robinson et al., Two-dimensional NMR spectroscopy in Earth's magnetic field, J. Magn. Res. 182 (2006) 343-347.

R. McDermott et al., Liquid-state NMR and scalar couplings in microtesla magnetic fields, Science 295 (2002) 2247-2249.

I.M. Savukov, M.V. Romalis, NMR detection with an atomic magnetometer, Phys. Rev. Lett. 94 (2005) 123001.

I.M. Savukov, S.J. Seltzer, M.V. Romalis, Detection of NMR signals with a radiofrequency atomic magnetometer, J. Magn. Res. 185 (2007) 214-220.

M.P. Ledbetter et al., Zero-field remote detection of NMR with a microfabricated atomic magnetometer, Proc. Natl. Acad. Sci. USA 105 (2008) 2286-2290.

S. Xu et al., Magnetic resonance imaging with an optical atomic magnetometer, Proc. Natl. Acad. Sci. USA 103 (2006) 12668-12671.

S. Xu et al., Submillimeter-resolution magnetic resonance imaging at the Earth's magnetic field with an atomic magnetometer, Phys. Rev. A 78 (2008) 013404.

D.B. Zax, A. Bielecki, K.W. Zilm, A. Pines, Heteronuclear zero-field NMR, Chem. Phys. Lett. 106 (1984) 550-553.

D.B. Zax, A. Bielecki, K.W. Zilm, A. Pines, D.P. Weitekamp, Zero field NMR and NQR, J. Chem. Phys. 83 (1985) 4877-4905.

V. Shah, S. Knappe, P.D.D. Schwindt, J. Kitching, Subpicotesla atomic magnetometry with a microfabricated vapor cell, Nat. Photonics 1 (2007) 649-652.

S. Knappe et al., Atomic vapour cells for chip-scale atomic clocks with improved long-term frequency stability, Optics Lett. 30 (2005) 2351-2353.

C.J. Lee, D. Suter, A. Pines, Theory of multiple pulse NMR at low and zero field, J. Magn. Res. 75 (1987) 110-124.

A. Llor, Z. Olejniczak, A. Pines, Coherent isotropic averaging in zero field NMR: 1. General theory and icosahedral sequences, J. Chem. Phys. 103 (1995) 3966-3981.

I.K. Kominis, T.W. Kornack, J.C. Allred, M.V. Romalis, A sub-femtoTesla multichannel atomic magnetometer, Nature 422 (2003) 596-599.

D. Budker, M.V. Romalis, Optical magnetometry, Nat. Phys. 3 (2007) 227-234.

Llor, A., Olejniczak, Z., & Pines, A. (1995b). Coherent Isotropic Averaging in Zero-Field Nuclear-Magnetic-Resonance .2. Cubic Sequences and Time-Reversal of Spin Couplings. Journal of Chemical Physics, 103(10), 3982-3997.

* cited by examiner

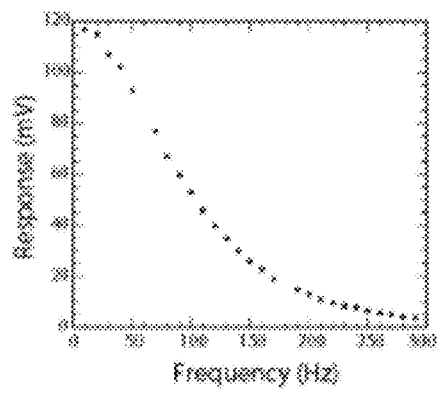 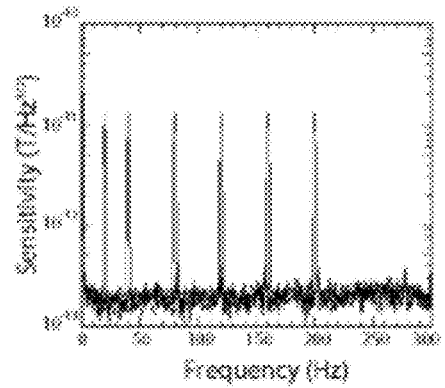
Fig. 2A  Fig. 2B
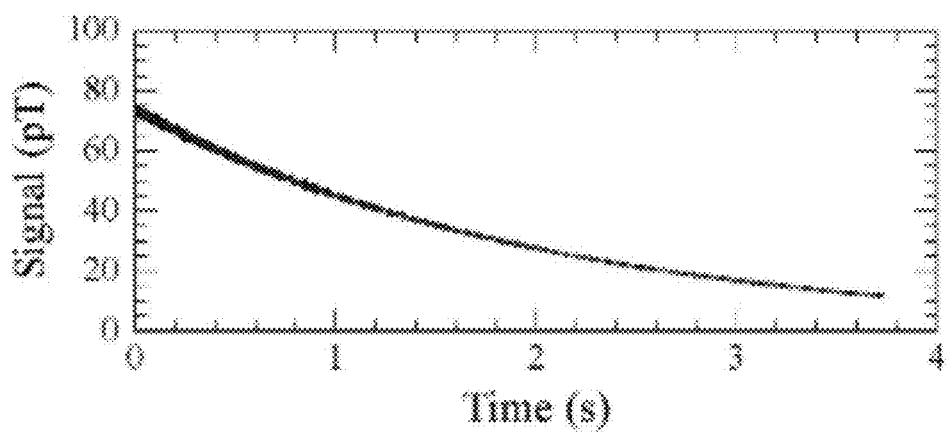
Fig. 3A
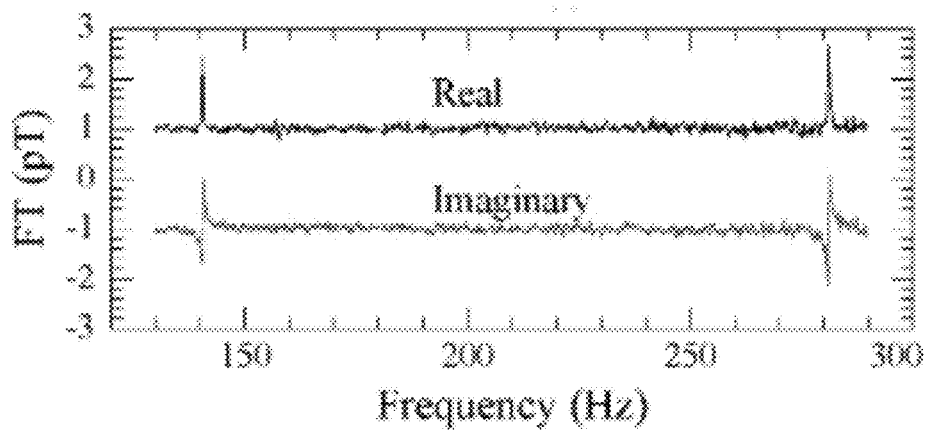
Fig. 3B

DETECTION OF J-COUPLING USING ATOMIC MAGNETOMETER

RELATED APPLICATIONS

This application is the national phase application of International application number PCT/US2010/030897, filed Apr. 13, 2010, which claims priority to and the benefit of U.S. Provisional Application No. 61/168,795, filed on Apr. 13, 2009, which is hereby incorporated by reference in its entirety.

STATEMENT OF GOVERNMENT SUPPORT

This invention was made with government support under Contract No. DE-AC02-05CH11231 awarded by the U.S. Department of Energy and with support from the National Institute of Standards and Technology, a non-regulatory agency within the U.S. Department of Commerce. The government has certain rights in this invention.

BACKGROUND OF THE INVENTION

The present invention relates to the field of nuclear magnetic resonance and, more particularly, to the field of detection of J- or scalar coupling.

Nuclear magnetic resonance (NMR) endures as one of the most powerful analytical tools for detecting chemical species and elucidating molecular structure. The fingerprints for identification and structure analysis are chemical shifts, nuclear Overhauser effects, and scalar couplings of the form $JI_1 \cdot I_2$. The latter yield useful information about molecular spin topology, bond and torsion angles, bond strength, and hybridization. NMR experiments are conventionally performed in high magnetic fields, requiring large, immobile, and expensive superconducting magnets. However, detection of NMR at low magnetic fields has recently attracted considerable attention in a variety of contexts, largely because it eliminates the need for superconducting magnets. Additional advantages of low and zero field NMR include extremely homogeneous fields (both spatially and temporally) for narrow lines and the appeal of measuring small contributions to the Hamiltonian in the absence of a much larger Zeeman interaction.

One-dimensional and two-dimensional spectroscopy (see, S. Appelt, H. Kühn, F. W. Häsing, B. Blümich, Chemical analysis by ultrahigh-resolution nuclear magnetic resonance in the Earth's magnetic field, *Nat. Phys.* 2 (2006) 105-109; and J. N. Robinson et al., Two-dimensional NMR spectroscopy in Earth's magnetic field, *J. Magn. Res.* 182 (2006) 343-347, respectively) have been demonstrated in the Earth's magnetic field using inductive detection. J-resolved spectra have been detected with superconducting quantum interference device (SQUID) magnetometers in ~µT fields (see, R. McDermott et al., Liquid-state NMR and scalar couplings in microtesla magnetic fields, *Science* 295 (2002) 2247-2249). Atomic magnetometers have been used to perform one-dimensional spectroscopy (see, I. M. Savukov, M. V. Romalis, NMR detection with an atomic magnetometer, *Phys. Rev. Lett.* 94 (2005) 123001; I. M. Savukov, S. J. Seltzer, M. V. Romalis, Detection of NMR signals with a radio-frequency atomic magnetometer, *J. Magn. Res.* 185 (2007) 214-220; and M. P. Ledbetter et al., Zero-field remote detection of NMR with a microfabricated atomic magnetometer, *Proc. Natl. Acad. Sci.* (USA) 105 (2008) 2286-2290) and for remote detection of magnetic resonance imaging in low magnetic fields. Nuclear magnetic resonance in a zero-field environment has been detected indirectly using field cycling techniques (see, D. B. Zax, A. Bielecki, K. W. Zilm, A. Pines, Heteronuclear zero-field NMR, *Chem. Phys. Lett.* 106 (1984) 550-553; and D. B. Zax, A. Bielecki, K. W. Zilm, A. Pines, D. P. Weitekamp, Zero field NMR and NQR, *J. Chem. Phys.* 83 (1985) 4877-4905). However, this practice does not remove the requirement for a superconducting magnet.

Low Field Nuclear Magnetic Resonance

Nuclear magnetic resonance (NMR), conventionally detected in multi-tesla magnetic fields, is a powerful analytical tool for the determination of molecular identity, structure, and function. With the advent of prepolarization methods and alternative detection schemes using atomic magnetometers or superconducting quantum interference devices (SQUIDs), NMR in very low-(~earth's field), and even zero-field, has recently attracted considerable attention. Despite the use of SQUIDs or atomic magnetometers, low-field NMR typically suffers from low sensitivity compared to conventional high-field NMR.

NMR[1,2] in low or zero magnetic field has long been viewed as a curiosity due to the low nuclear spin polarization, poor sensitivity of inductive pickup coils at low frequencies, and the absence of site-specific chemical shifts.

Despite the use of atomic magnetometers or SQUIDS, low-field NMR using samples thermally prepolarized in a permanent magnet typically suffers from low signal-to-noise ratio compared to inductively-detected high-field NMR, in part because of the low polarization available from thermalization in a permanent magnet.

While parahydrogen induced polarization (PHIP) has been investigated in a variety of magnetic fields, ranging from the earth's field to high field, observation of the resulting NMR signals has always been performed in finite magnetic field.

SUMMARY OF THE INVENTION

An embodiment of a method of detecting a J-coupling of the present invention includes providing a polarized analyte adjacent to a vapor cell of an atomic magnetometer and measuring one or more J-coupling parameters using the atomic magnetometer. According to an embodiment, measuring the one or more J-coupling parameters includes detecting a magnetic field created by the polarized analyte as the magnetic field evolves under a J-coupling interaction.

BRIEF DESCRIPTION OF THE DRAWINGS

The present invention is described with respect to particular exemplary embodiments thereof and reference is accordingly made to the drawings in which:

FIGS. 2A and 2B provide graphs that show the response of an atomic magnetometer to test fields of varying frequency and the noise floor of the magnetometer, respectively.

FIGS. 3A and 3B provide graphs of a raw signal and a Fourier transform of the raw signal, respectively, which were obtained with a sample of $^{13}C$ enriched methanol following an excitation pulse with area $B_1 T_p(\gamma_H - \gamma_C) = 2.4$ rad.

DETAILED DESCRIPTION OF THE INVENTION

Scalar couplings of the form $JI_1 \cdot I_2$ between nuclei impart valuable information about molecular structure to nuclear magnetic-resonance spectra. Examples of the present invention demonstrate direct detection of J-spectra due to both heteronuclear and homonuclear J-coupling in a zero field environment, where the Zeeman interaction is completely absent. It is shown here that characteristic functional groups exhibit distinct spectra with straightforward interpretation for chemical identification. Detection is performed with a microfabricated optical atomic magnetometer, providing high sensitivity to samples of microliter volumes. In examples of the present invention, linewidths of 0.1 Hz were obtained and scalar-coupling parameters with 4-mHz statistical uncertainty were measured. It is anticipated that the technique described here may provide a new modality for high-precision "J spectroscopy" using small samples on microchip devices for multiplexed screening, assaying, and sample identification in chemistry and biomedicine.

The present invention provides for the direct detection of hetero- and homonuclear scalar coupling in a zero field environment or a low field environment using an optical atomic magnetometer. Examples of the present invention show that characteristic functional groups have distinct spectra, with straightforward interpretation for molecular structure identification, allowing extension to larger molecules and to higher dimensional Fourier NMR spectroscopy. A magnetically shielded, zero field environment provides high absolute field homogeneity and temporal stability, which provides a capability to obtain 0.1-Hz linewidths without using spin echoes, and to determine scalar coupling parameters with a statistical uncertainty of 4 mHz. Such linewidths and measurement uncertainties are far better than were previously available for J-coupling measurements, providing a super-sensitive means for detection of subtle differences in chemical structure.

As used herein, the term "zero field" refers to a static magnetic field having a zero or near-zero magnitude in which the magnetic field is small enough that the larmor precession frequency is small. For a sample with protons, a smallest competing timescale is the relaxation rate, so that the precession frequency should be less than $1/(2\pi T_2)$ or ~100 mHz, corresponding to about 2.5 nT. Thus, a zero field includes a static magnetic field of 0.1 nT or an oscillating magnetic field with a near zero average magnitude. As used herein, the term "low field" refers to a static magnetic field having a magnitude less than about 1 mT and more typically less than about 100 μT. Zero field and low field are in contrast to high field (i.e. a static magnetic field having a high magnitude), where a typical high field in the context of NMR has a magnitude on the order of 3 to 10 T.

Figure 1:
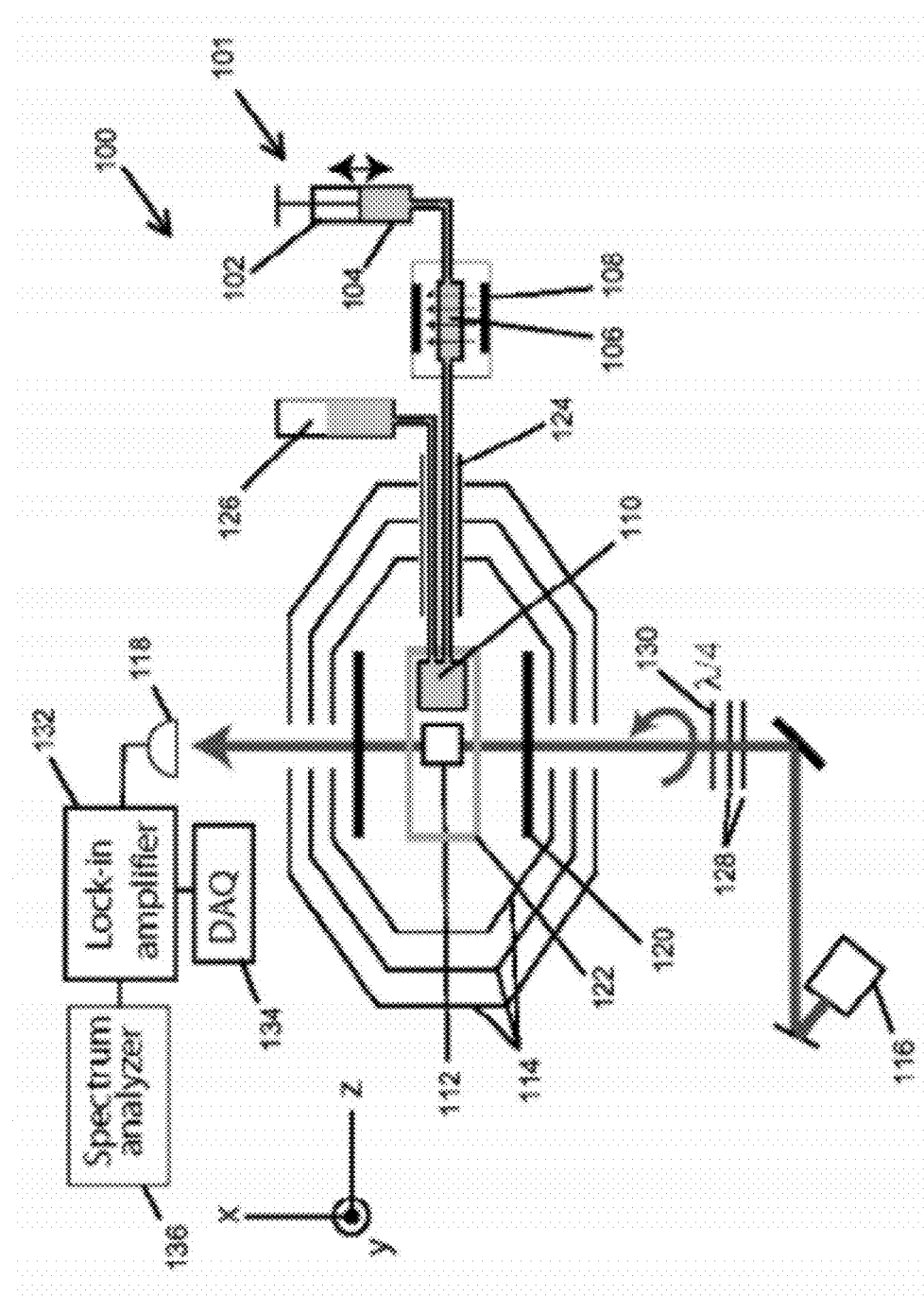
FIG. 1 illustrates a system 100 for detecting J-coupling in accordance with an embodiment of the present invention.

An embodiment of a system for detecting J-coupling in accordance with an embodiment of the present invention is illustrated in FIG. 1. The system 100 includes an optical atomic magnetometer, a fluid handling system 101, magnetic shields 114, coils 120, and an oven 122. According to an embodiment, the atomic magnetometer includes a laser 116 (e.g., an external-cavity diode laser that produce light at the D1 resonance), an alkali vapor cell 112 (e.g., an $^{87}$Rb alkali-vapor cell), a photo-diode 118, a lock-in amplifier 132, polarizers 128, and a quarter wave plate 130. According to an embodiment, the fluid handling system 101 includes a syringe pump 102, a reservoir 104, a polarization volume 106, a Halbach array 108 (e.g., 1.8-T Halbach array), a solenoid 124, a detection volume 110 (e.g., an 80-μL detection volume), and a pressurized reservoir 126.

In operation, the syringe pump 102 pushes fluid from the reservoir 104 into the polarization volume 106, which is within the Halbach array 106, and then into the detection volume 110, which is adjacent to the alkali-vapor cell 112. The vapor cell 112 and the detection volume 110 are housed within the oven 122, which is inside the set of magnetic shields 114. Circularly polarized light from the external-cavity diode laser 116 at the D1 resonance is used to optically pump and probe the alkali spin polarization within the vapor cell 112. The circularly polarized light that passes through the vapor cell 112 is detected by the photodiode 118. The set of coils 120 inside the magnetic shields 114 is used to zero the residual magnetic field, apply pulses to the sample in the y-direction, and to oscillate a small magnetic field in the z-direction. The oven 122 heats the vapor cell 112 to ~170° C. to maintain sufficient alkali vapor density. The detection volume 110 may be separated from the vapor cell 112 by a gap so that it operates at a lower temperature than the vapor cell 112. Also, the detection volume 110 may be cooled, for example, by attaching it to a heat sink that is outside of the oven 122. In an alternative embodiment, the oven 122 is replaced by a heat source that is attached to the vapor cell 112. The solenoid 124 provides a quantizing magnetic field (about 50 μT) to help maintain the orientation of the polarization of the analyte as it is transferred from the polarization volume 106 to the detection volume 110. The pressurized reservoir 126 receives the analyte after it has been analyzed in the detection volume 110. Linear polarizers 128 are used to polarize light from the laser 116. A quarter wave plate 130 circularly polarizes the laser light. A lock-in amplifier 132 detects the signal from the photodiode 118. A data acquisition system 134 may record the signal from the photodiode 118. A spectrum analyzer 136 may be used to view the data acquired in experiments.

An embodiment of a method of detecting a J-coupling of the present invention includes providing a polarized analyte adjacent to the vapor cell 112 of the atomic magnetometer and measuring one or more J-coupling parameters using the atomic magnetometer. According to an embodiment, a fluid analyte is polarized in a strong magnetic field (e.g., the Halbach array 108), which produces the polarized analyte, and then the polarized analyte flows into the detection volume 110 within a zero field region adjacent to the vapor cell 112 of the atomic magnetometer. Pulses can then be applied to prepare a superposition of eigenstates of the J-coupling Hamiltonian, which then evolve freely, without influence of any external field, producing a time dependent magnetization. The magnetic field from the polarized sample is detected by the atomic magnetometer. Advantages of working in a zero field environment include a homogeneous field and temporal stability.

According to an embodiment of the present invention, the atomic magnetometer works as follows. A single, circularly polarized laser beam optically polarizes orientation in the ground state of the alkali atoms enclosed in the vapor cell 112. A fully polarized vapor is transparent to the circularly polarized light. A small magnetic field applied to the alkali vapor induces precession of the oriented alkali vapor about the magnetic field, reducing the intensity of the transmitted light which is monitored by the photodiode, thereby producing a measure of the magnetic field. To move away from low frequency noise, a 1.8 kHz modulation of the magnetic field is applied, with amplitude of about 15 nT. This results in modulation of the transmitted light at the second harmonic. An offset in the magnetic field from the J-coupling of the polarized analyte results in a first harmonic, which is detected by the lock-in amplifier. The amplitude of the modulation field is sufficiently small and the oscillation frequency sufficiently fast that their effect on the nuclei to be measured averages to zero. It is emphasized that the single beam embodiment discussed here and shown in FIG. 1 is only one possibility. Other embodiments using two beams to pump and probe either orientation or alignment of the alkali vapor, each with various advantages, are possible. In the implementation depicted in FIG. 1, the magnetometer is sensitive to the z component of the magnetic field. Since the line from the sample to the detection volume lies along the z direction, it is the z component of the magnetization which is detected.

In the implementation discussed here, polarization of the sample is produced via thermalization in a large magnetic field in a remote location (e.g., the Halbach array 108). However, other methods of polarization are possible, such as spin-exchange optical pumping, para-hydrogen induced polarization, or dynamic nuclear polarization. Regardless of the prepolarization method, high sensitivity is achieved by the close proximity of the vapor cell 112 to the detection volume 110.

According to an embodiment of the present invention, scalar coupling is accomplished as follows. Polarized fluid flows into the detection volume 110 in a zero field environment. A pulse of DC current is applied to one or more of the coils 120, which applies a magnetic field pulse that rotates spins with different gyromagnetic ratios by different angles about the magnetic field pulse. This places the system in a superposition of eigenstates of the J-coupling Hamiltonian, leading to quantum beats. Evolution due to the J-coupling Hamiltonian produces a modulation of the z component of the magnetization at the quantum beat frequencies, which is then detected by the magnetometer.

In another embodiment, an additional laser can be employed, yielding approximately a factor of 10 improvement in sensitivity. In this alternative configuration, and with reference to FIG. 1, this second, pump laser is circularly polarized and propagates in the y direction (out of the page). In this embodiment, the pump laser passes through polarizers and a quarter wave plate the same as polarizers 128 and quarter wave plate associated with diode (i.e. probe) laser 116. The pump laser is tuned to the center of the pressure broadened D1 transition of $^{87}$Rb. This polarizes the atoms along the direction of the pump beam propagation. In this arrangement, quarter wave plate 130 is removed from laser 116, which facilitates tuning of the two lasers, the probe laser now linearly polarized, propagating in the x direction, and tuned two or three pressure broadened line widths off resonance. In the presence of a magnetic field in the z direction, the alkali spins rotate into the x direction. This produces optical rotation of the probe beam. This optical rotation can be detected using a balanced polarimeter consisting of a Wollaston prism (other polarizing beam splitters could work as well) and two photodiodes.

Figure 6:
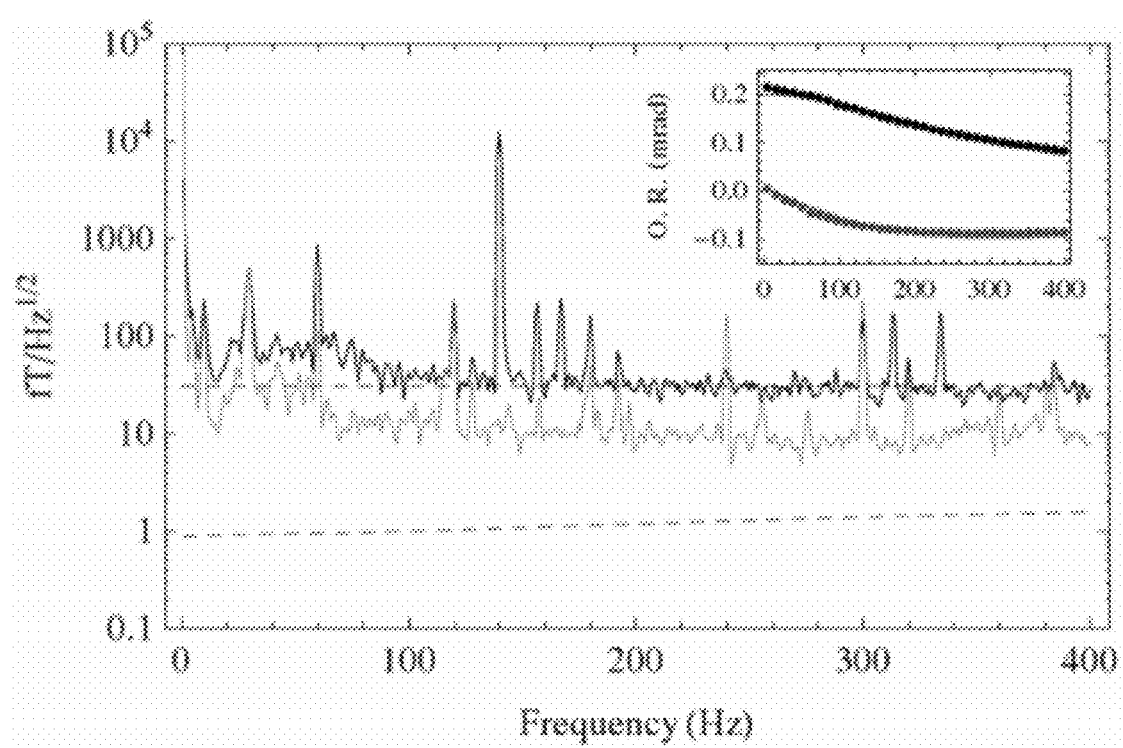
FIG. 6 is a plot of noise as a function of frequency, the smaller plot insert in the main panel shows the optical response vs. frequency for an alternative arrangement where a second, pump laser has been employed along with a first, probe laser.

Operational results for the two laser arrangement are shown at FIG. 6, which in the larger box depicts the sensitivity of the magnetometer as a function of noise vs. frequency. The darker trace shows the actual magnetic field noise of the magnetometer, the lighter trace shows optical noise of the probe beam when the pump beam is blocked. The smaller insert is a plot of optical response vs. frequency, the upper line a plot for in phase responses, the lower line a plot for out of phase responses.

The use of atomic magnetometers yields greatly improved sensitivity compared to inductive detection at low- or zero-magnetic field because the atomic magnetometers sense magnetic field directly, rather than the time derivative of flux through a pickup coil. Furthermore, in contrast to SQUIDS, atomic magnetometers do not require cryogenics. Examples of the present invention achieved efficient coupling to small samples by making use of millimeter-scale magnetometers (see, V. Shah, S. Knappe, P. D. D. Schwindt, J. Kitching, Subpicotesla atomic magnetometry with a microfabricated vapor cell, *Nature Photonics* 1 (2007) 649-652) manufactured using microfabrication techniques (see, S. Knappe et al., Atomic vapour cells for chip-scale atomic clocks with improved long-term frequency stability, *Optics Letters* 30 (2005) 2351-2353). Examples of the present invention employed an 80-μL detection volume. Examples of the present invention also used magnetic shielding, which permits operation in a laboratory environment, where perturbations to the Earth's magnetic field may limit the magnetic field homogeneity and stability.

Operation at zero field eliminates the chemical shift but retains substantial analytical information in simplified spectra determined by both heteronuclear and homonuclear scalar couplings. The $^{13}CH_3$ group provides an example of the simplification afforded by spectroscopy in a zero field environment. The Earth's field spectrum consists of eight lines (see, S. Appelt, F. W. Häsing, H. Kuhn, B. Blümich, Phenomena in J-coupled nuclear magnetic resonance spectroscopy in low magnetic fields. *Phys. Rev. A* 76 (2007) 023420), while, as shown here, the zero-field spectrum consists of just two lines, without loss of spectral and analytical information. It is believed that this will facilitate controllable extension into multidimensional spectroscopy with the incorporation of zero-field decoupling and recoupling sequences (see, C. J. Lee, D. Suter, A. Pines, Theory of multiple pulse NMR at low and zero field, *J. Magn. Res.* 75 (1987) 110-124; and A. Llor, Z. Olejniczak, A. Pines, Coherent isotropic averaging in zero field NMR: 1. general theory and icoshedral sequences, *J. Chem. Phys.* 103 (1995) 3966-3981).

Nuclear magnetic resonance is a powerful analytical tool for determination of molecular structure and properties. There are generally a number of terms in the NMR Hamiltonian that can be used for understanding molecular structure, including the Zeeman interaction, dipole-dipole coupling, quadrupole coupling, and scalar coupling discussed here. While operation at zero field eliminates the Zeeman interaction, all other terms in the NMR Hamiltonian remain. The present invention demonstrates that it is possible to detect the scalar coupling interaction in a zero field environment. Scalar couplings yield information about the presence of covalent bonds, bond angle, torsion, and strength. As a more "blunt instrument", they could be used as a marker to determine if a reaction has occurred, for example, to see if a drug molecule has bound to the appropriate receptor. If used to monitor the products of a reaction, catalyzed by enzymes or microreactors, J-couplings could be used to optimize the performance of the catalyst.

The present invention could be widely used in both pure research environments, as well as industry. For example; the invention could be used to evaluate the effectiveness of an experimental catalyst by monitoring covalent bonds in the product of the reaction. The pharmaceutical industry could be potentially interested in this invention because it may aid in drug discovery programs by providing a tool to monitor whether a drug molecule has bound to a receptor. More generally, the present invention may find application in a chemical production facility by monitoring concentrations of reactants, products, or un-wanted by-products, where such process information may be used to adjust process parameters.

The present invention may also find applications in security monitoring, for example, in the detection of liquid hydrocarbons, which often have more energy per unit mass than TNT. While an existing technique for detection of solid explosive compounds employs NQR (nuclear quadrupole resonance) spectroscopy, it does not work for liquids. One particular security monitoring application may be in an airport screening machine that detects liquid explosives by finding a recognized J-coupling spectra.

At zero magnetic field, the Hamiltonian for a network of spins coupled through scalar interactions is $$H_J = \hbar \Sigma J_{jk} I_j \cdot I_k, \quad (Eq. 1)$$

where the sum extends over all distinct spin pairs and $J_{jk}$ is the J-coupling parameter for spins j and k. The observable in the present invention is the z component of the magnetization of the sample (see Experimental section below), $$M_z(t) = \hbar n Tr\left(\rho(t) \sum_j \gamma_j I_{j,z}\right), \quad (Eq. 2)$$

where n is the number density of molecules, $\gamma_j$ is the magnetogyric ratio of the j-th spin, and $\rho(t)$ is the density matrix. The temporal evolution of an arbitrary system of spins can be determined by diagonalizing the Hamiltonian to find the eigenstates $|\phi_a\rangle$ and eigenvalues $E_a$, and expressing the initial density matrix as a sum of the operators $|\phi_a\rangle\langle\phi_b|$, each of which evolves as $e^{i\omega_{ab}t}$, where $\omega_{ab}=(E_a-E_b)/\hbar$.

Because $I_{j,z}$ are vector operators with magnetic quantum number zero, observable coherences are those between states that differ by one quantum of total angular momentum F, $|\Delta F|=1$ with $\Delta M_F=0$. This selection rule can be used for prediction of the positions of peaks and for interpretation of spectra. For instance, consider the case of $^{13}CH_N$, where the J-coupling $J_{CH}$ between all N heteronuclear pairs is identical. Since the protons are all equivalent, the homonuclear J-couplings can be ignored (see ref 2). Denoting the total proton spin by K and the $^{13}$C spin by S, Eq. (1) can be rewritten $H_J = \hbar J_{HC} K \cdot S$, which has eigenstates $|F^2, K^2, S^2, F_z\rangle$ with eigenvalues $$E_{F,K} = \hbar \frac{J_{HC}}{2}[F(F+1) - K(K+1) - S(S+1)]. \quad (Eq. 3)$$

The selection rules above yield the observable quantum-beat frequencies $\omega_K=(E_{K+1/2,K}-E_{K-1/2,K})/\hbar=J_{HC}(K+½)$ for $K \geq ½$. For the methyl group, $^{13}CH_3$, two lines are expected, one at $J_{HC}$ and another at $2J_{HC}$, corresponding to coupling of the $^{13}$C nucleus with the proton doublet or quadruplet states. For the methylene group, $^{13}CH_2$, a single line at $3J_{HC}/2$ is expected due to coupling with the proton triplet state. In more complicated molecules, homonuclear couplings or higher-order effects of heteronuclear couplings can result in a splitting of the lines—however, the positions of the multiplets can be determined by the above argument.

Experimental:

A schematic of the zero-field spectrometer 100 is shown in FIG. 1. The detection volume 110 and the vapor cell 112 of the optical-atomic magnetometer are housed inside a set of magnetic shields 114 and coils 120 to create a zero-field environment to a level of 0.1 nT. A syringe pump 102 cycles fluid analyte between the polarization volume 106 and the 80-μL detection volume 110 via a 50-cm long tube with inner diameter of 250 μm. The prepolarizing volume is placed in a compact (5 cm×5 cm×10 cm) 1.8-T Halbach array 108. A pressurized reservoir 126 aids refilling the syringe on the refill cycle. The flow rate is 50 μL/s, yielding an average fluid velocity of 100 cm/s and transit time of 0.5 s from magnet to detection region (small compared to the longitudinal relaxation rate of the samples measured here). A solenoid 124 provides a "guiding field" in transit from the ambient laboratory field to zero field to ensure that the initial magnetization points towards the atomic magnetometer.

The central component of the magnetometer is a vapor cell, with inner dimensions 2.7 mm×1.8 mm×1 mm, containing $^{87}$Rb and 1200 Torr of $N_2$ buffer gas, fabricated using the techniques described by Knappe et al in *Optics Letters*. The atomic magnetometer operates in the spin-exchange relaxation-free (SERF) regime (see, I. K. Kominis, T. W. Kornack, J. C. Allred, M. V. Romalis, A sub-femtoTesla multichannel atomic magnetometer, *Nature* 422 (2003) 596-599), in which relaxation of the alkali polarization due to spin-exchange collisions is eliminated. As described by Shah et al. in *Nature Photonics*, a single circularly polarized laser beam is used here, which is tuned to the center of the pressure broadened Rb D1 transition, propagating in the x direction, to optically pump and probe the alkali polarization. A magnetic field in the z direction rotates the alkali polarization away from the direction of light propagation, and correspondingly, the absorption of the light increases. In order to avoid interference from low-frequency noise, a modulation of the z component of the magnetic field is applied at a frequency $\nu_{mod}$=1.8 kHz, with amplitude similar to the width of the alkali Zeeman resonance (about 15 nT in the vapor cell used here). The z component of the magnetic field due to the sample leads to modulation of the transmitted light at the first harmonic of the modulation frequency, which is monitored with the lock-in amplifier 132. FIG. 2A shows the response of the magnetometer to a small oscillating test field as a function of frequency. FIG. 2B shows the sensitivity of the magnetometer (the sharp peaks are for calibration) after normalizing the measured noise and calibration signals by the frequency response of the magnetometer, yielding a noise floor of about 200 fT/√Hz, flat from about 3 Hz to 300 Hz.

Data presented in this work was acquired as follows: Fluid polarized by the Halbach array 108 flows into the detection volume 110, and at t=0, flow is halted and a pulse of DC magnetic field is applied in the y direction with magnitude $B_1$ and duration $T_p$. This rotates the proton and $^{13}$C spins by different angles due to the different magnetogyric ratios, placing the spin system into a superposition of eigenstates of the J-coupling Hamiltonian, Eq. (1). The ensuing quantum beats lead to a time-dependent magnetization, the z component of which is detected by the atomic magnetometer. The transfer of the sample from high field to zero field is adiabatic as no quantum beats are observed without application of an excitation pulse. Adiabatic transfer results in equilibration of the spin-temperature parameters of the two species via the J-coupling interaction, the initial condition for simulations presented below.

Experiments were performed with $^{13}$C enriched methanol ($^{13}CH_3$—OH), ethanol 1 ($^{12}CH_3$—$^{13}CH_2$—OH), and ethanol 2 ($^{13}CH_3$—$^{12}CH_2$—OH) obtained from Cambridge Isotope Laboratories. Methanol and ethanol 2 data were acquired with no further sample preparation. Ethanol 1 data were acquired following several freeze-thaw cycles under vacuum to help remove any dissolved gases, e.g. $O_2$, however the linewidth and longitudinal relaxation time was similar for ethanol 1 and ethanol 2.

Results and Discussion:

Measurements on methanol, $^{13}CH_3OH$, are presented in FIGS. 3A and 3B for a pulse area $\alpha=B_1 T_p(\gamma_H-\gamma_C)$=2.4 rad ($T_p$=0.66 ms). The signal in the time domain after averaging 11 transients is shown in FIG. 3A. There is a large, slowly decaying component of the signal due to the relaxation of static components of the total magnetization, as well as a smaller, high frequency component due to scalar coupling. Overlaying the data is a decaying exponential with time constant $T_1$=2.2 s. In displaying these data, the decaying exponential was first subtracted, filtered the remaining signal with a pass band between 120 and 300 Hz and then added the decaying exponential to the filtered data. This eliminates transients at the beginning and end of the data set due to the digital filter. The Fourier transform of the signal is shown in FIG. 3B after correcting for the finite bandwidth of the magnetometer, revealing a simple structure consisting of two peaks (offsets inserted for visual clarity). This spectrum is in agreement with the discussion of $^{13}CH_3$ given above, assuming that the homo- and heteronuclear coupling of the OH group are averaged to zero under rapid chemical exchange. Independently fitting the low- and high-frequency portions of the data to complex Lorentzians yields central frequencies $v_1=140.60$ Hz and $v_2=281.09$ Hz with linewidths (half-width at half-maximum) $\Delta v_1=0.10$ Hz and $\Delta v_2=0.17$ Hz. These values are in agreement with the value found in the literature of $J_{HC}=140.6$ Hz for methanol.

Figure 4A:
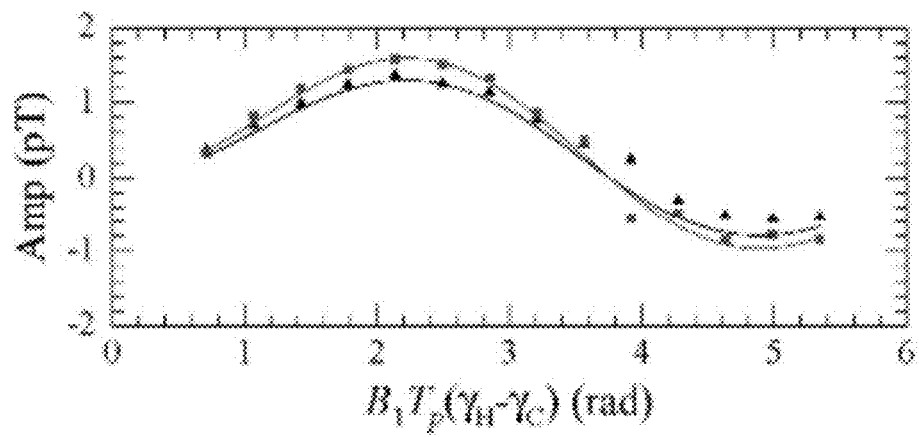
FIGS. 4A and 4B provide graphs of J-coupling data for methanol.

The amplitudes of the low- and high-frequency peaks as a function of pulse area are shown by triangles and squares, respectively in FIG. 4A. Using the formalism discussed above, one can show that if the polarized part of the density matrix prior to the excitation pulse is of the form $$\rho = \beta \sum_j I_{j,z},$$

the amplitude of the two resonances is given by $$A_1 = 2(\gamma_c - \gamma_h)\sin(B_1 T_p(\gamma_h + \gamma_c))\sin(B_1 T_p(\gamma_h - \gamma_c)), A_2 = 5A_1/4 \quad \text{(Eq. 4)}$$

The lines overlying the data are theoretical predictions, in agreement with the data. This dependence can be understood as follows: Following the pulse, the protons and $^{13}C$ nuclei precess around the total angular momentum F, and hence the time dependent magnetization is produced in a direction transverse to F. The projection of the transverse component of F along the z axis following the pulse is modulated according to $\sin B_1 T_p(\gamma_h + \gamma_c)$, and the amplitude of the time dependent part of the magnetization transverse to F is determined by the phase difference accrued by protons and $^{13}C$ nuclei during the pulse, yielding the final $\sin B_1 T_p(\gamma_h - \gamma_c)$ factor in Eq. 4.

In FIG. 3A, there is a slowly decaying exponential with a time constant $T_1=2.2$ s, and on top of this, a smaller, oscillating signal due to coupling of the $^{13}C$ with the protons. The real and imaginary parts of the spectrum are represented in FIG. 3B by the upper and lower traces, respectively. The low-frequency and high-frequency peaks correspond to the coupling of the $^{13}C$ nucleus with the doublet and quadruplet states of proton angular momentum, respectively.

In order to determine the stability of the J-coupling measurement, a series of 100 transients were acquired following the application of a pulse with area $\alpha=2.4$ rad, the first maximum of the response in FIG. 4A. The raw data were binned into sets of ten, averaged, Fourier transformed, and fit to complex Lorentzians. The position of the low-(triangles) and high-(squares) frequency peaks are shown as a function of bin number in FIG. 4B. The mean frequencies of each peak are indicated by the solid lines overlaying the data with $v_1=140.566(4)$ Hz and $v_2=281.082$ (3) Hz. As mentioned above, these values appear to be in agreement with the value found in the literature, however, these data deviate slightly from the $^{13}CH_3$ model discussed above because $v_2/2$ differs from $v_1$ by about 25 mHz. It is suspected that this small shift is the result of residual coupling to the OH group, and simulation indicates that it would require a coupling of only 0.4 Hz to produce a shift of this magnitude and sign. The statistical uncertainties in these measurements are orders of magnitude smaller than the range of frequencies associated with J-couplings, providing a sensitive probe for subtle differences in chemical structure.

Figure 4B:
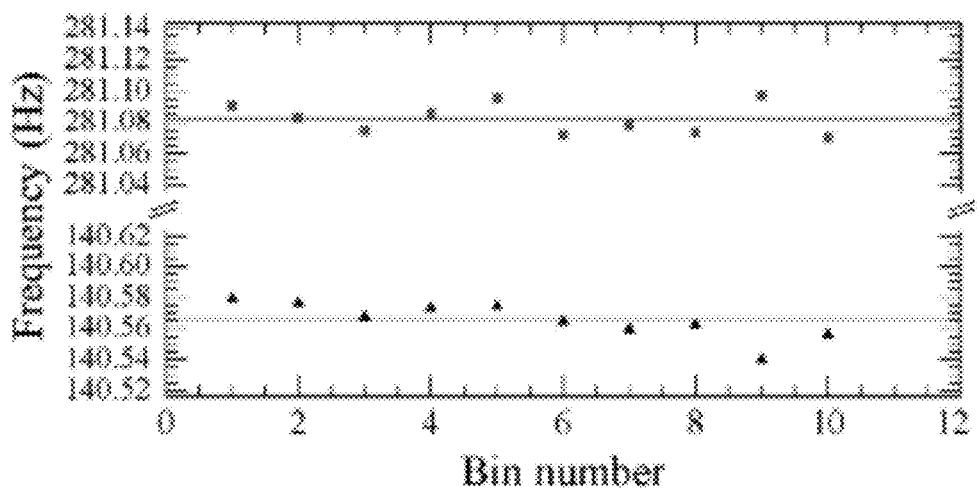

In FIG. 4A, triangles and squares show the dependence of the amplitude of the low-and high-frequency resonances in $^{13}C$ enriched methanol on pulse area, respectively. The solid lines overlaying the data are theoretical predictions in FIG. 4A. In FIG. 4B, the center of the low (triangles) and high (squares) frequency resonances as a function of bin number, each bin consisting of the average of 10 transients. From these data, the mean value of the central frequency for the two peaks was determined to be 140.566(4) and 281.082(3) Hz, as indicated by the solid lines overlaying the data.

Figure 5A:
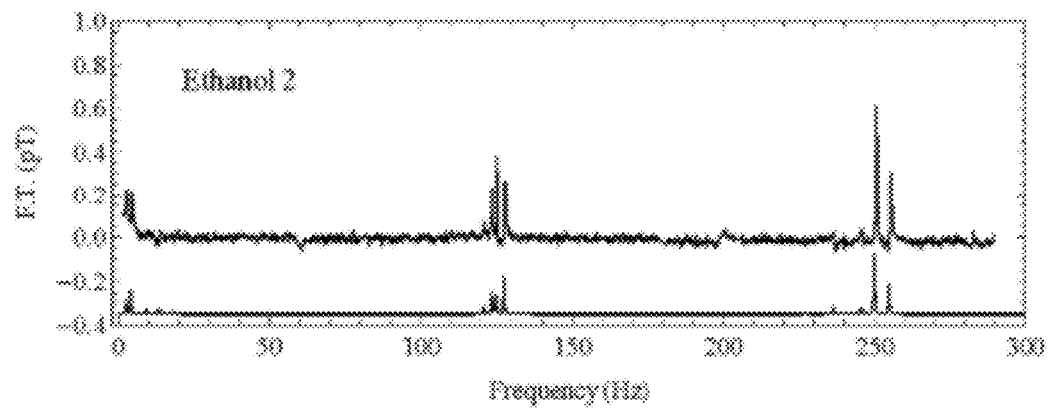
FIGS. 5A and 5B provide graphs of experimental and simulated zero-field NMR spectra for ethanol 2 ($^{13}CH_3$—$^{12}CH_2$—OH) and ethanol 1 ($^{12}CH_3$—$^{13}CH_2$—OH), respectively.
Figure 5B:
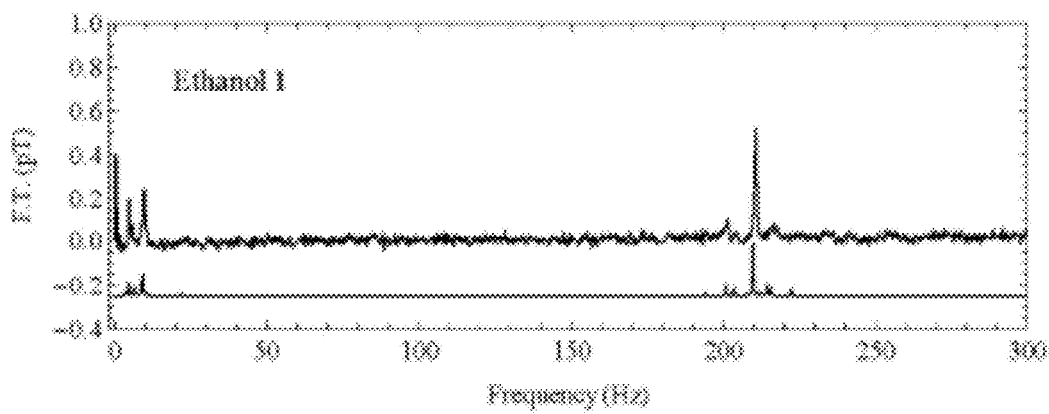

As mentioned above, homonuclear J-coupling between equivalent spins cannot be observed. In high-field NMR experiments, this is often overcome by differences in chemical shift between different functional groups. At low or zero magnetic field, where chemical shifts are unresolved or nonexistent, homonuclear non-equivalence can occur through different heteronuclear J-coupling environments (see, e.g., ref 15). For example, in ethanol 1, $^{12}CH_3$—$^{13}CH_2$—OH, or ethanol 2, $^{13}CH_3$—$^{12}CH_2$—OH, the protons in the methyl and methylene groups couple to the $^{13}C$ nucleus differently, yielding observable effects due to homonuclear J-coupling. FIGS. 5A and 5B show experimental spectra for ethanol 2 and ethanol 1, obtained after averaging 475 and 210 transients, respectively. Simulated spectra, presented below the data, are in agreement with experiment. In the simulations, the values of coupling constants obtained from high-field measurements were used, which, for ethanol 1 are $J_{HC}^{(1)}=140.4$ Hz, $J_{HC}^{(2)}=-4.6$ Hz and $J_{HH}^{(3)}=7.1$ Hz and for ethanol 2 are $J_{HC}^{(1)}=125.2$ Hz, $J_{HC}^{(2)}=-2.4$ Hz and $J_{HH}^{(3)}=7.1$ Hz, where the superscript denotes the number of bonds separating the interacting nuclei. These spectra can be interpreted as follows: The Hamiltonian is dominated by the one-bond heteronuclear J-coupling. Hence, neglecting any other couplings, for ethanol 1, one expects a single peak at $3J_{HC}^{(1)}/2$ due to coupling between the $^{13}C$ nucleus and the triplet proton state of the methylene group. In ethanol 2, one expects two peaks at $J_{HC}^1$ and $2J_{HC}^1$ due to coupling between the $^{13}C$ nucleus and the doublet or quadruplet states of the protons on the methyl group. Homonuclear couplings and two-bond heteronuclear couplings result in a splitting of these peaks, as well as the appearance of a set of peaks at low frequencies.

As shown in FIG. 5, to the extent that the signal is above the noise level, experiment and simulation are in agreement. The positions of the multiplets are determined by the one-bond heteronuclear J-coupling and the splittings within the multiplets are due to homonuclear J-coupling and two-bond heteronuclear J-coupling.

Simulation and further experimental results not presented here indicate that spectra rapidly become quite complex in molecules such as doubly labeled ethanol, where there are multiple one-bond heteronuclear and homonuclear couplings. Future work is planned to explore methods for selective and broadband decoupling of heteronuclear scalar couplings for simplification of zero field spectra. Compounds containing nitrogen (present in many biologically relevant molecules) can be labeled with $^{15}N$ which will provide an additional means for manipulating the nuclear spin Hamiltonian. Lastly, while the present results were obtained in a zero field environment, spectral features in the complementary low field (~50 µT) regime can also be observed with an atomic magnetometer. As demonstrated Savukov et al. in *J. Magn. Res.*, atomic magnetometers can also be used for direct detection of NMR in finite fields.

Finally, in the present work, the magnetometric sensitivity is about 200 fT/√Hz, with a vapor cell volume of about 4.8 mm³. Laser intensity fluctuations are the dominant source of noise and are about a factor of 50 larger than photon shot noise. A straightforward path to improved sensitivity would be to incorporate a second, low noise laser, and monitor optical rotation, which would cancel common mode noise.

Fundamentally limiting the sensitivity of an atomic magnetometer is spin-projection noise (see, D. Budker, M. V. Romalis, Optical Magnetometry, *Nature Physics* 3 (2007) 227-234), and in Ledbetter et al., *Proc. Natl. Acad. Sci.*, it was estimated that, for millimeter-scale vapor cells with optimal values of parameters such as light power, cell temperature, and buffer gas pressure, spin-projection noise is on the order of 0.1 fT/√Hz, indicating that there is still a great deal of room for improved magnetometric sensitivity. Hyperpolarization techniques such as dynamic nuclear polarization or parahydrogen-induced polarization can also be employed to yield much larger signals, making possible the detection of natural-abundance samples.

In conclusion, direct detection of pure J-coupling NMR at zero magnetic field using an optical atomic magnetometer has been demonstrated. For characteristic functional groups, such as $^{13}CH_3$, the zero-field spectrum is simpler than Earth-field spectra while retaining all information about the J-coupling network. Linewidths as low as 0.1 Hz were obtained, heteronuclear J-coupling constants with 4-mHz statistical uncertainty were measured, and homonuclear J-coupling was clearly observed. Zero-field relaxation rates can also easily be measured with only a single pulse. The sensitivity is sufficient to obtain simple spectra from 80 μL of fluid in a single shot. Further optimization of magnetometric sensitivity and geometry is expected to yield improved performance with detection volumes at the level of 1 μL. It is anticipated that the technique described here will find wide use in analytical chemistry. Applications to multiplexed screening, assaying and identification of samples from chemistry to biomedicine with mobile, miniaturized devices are also envisaged. One particular application that is envisioned is in monitoring changes of scalar couplings in the products of enzyme catalyzed reactions.

Parahydrogen Enhanced Zero-Field Nuclear Magnetic Resonance

The present invention provides direct detection of zero-field NMR signals generated via parahydrogen induced polarization (PHIP), enabling high-resolution NMR without the use of any magnets. The sensitivity is sufficient to observe spectra exhibiting $^{13}C$—$^{1}H$ scalar nuclear spin-spin couplings (the so-called J-couplings) in compounds with $^{13}C$ in natural abundance in a single transient. The resulting spectra display distinct features that have straightforward interpretation and can be used for chemical fingerprinting.

The present invention removes the obstacles of low nuclear spin polarization and poor sensitivity of inductive pickup coils at low frequencies. The present invention can obtain high-resolution, high signal-to-noise ratio, zero-field NMR spectra that are rich in information. This facilitates the development of portable sensors for chemical analysis and imaging by elimination of cryogenically cooled superconducting magnets. Additionally, working in low or zero magnetic-field yields narrow lines and accurate determination of line positions, due to the high absolute field homogeneity and stability. These features have enabled chemical analysis via $^{129}Xe$ chemical shifts[3] and spin-spin or J-couplings between $^{1}H$—$^{13}C$, $^{1}H$—$^{29}Si$, and $^{1}H$—$^{19}F$ in low- or zero-magnetic field[4, 5, 6]. Atomic magnetometers[7,8] and SQUIDs[9] are sensitive to low-frequency signals, offering dramatically improved signal-to-noise ratio (compared to inductive pickup coils) in low-field NMR[4, 10, 11] and magnetic resonance imaging[12,13].

To avoid low polarization available from thermalization in a permanent magnet difficulty, the present invention could produce large nuclear spin polarization in zero-field NMR by employing the technique of parahydrogen induced polarization (PHIP), whereby order from the singlet state of parahydrogen is transferred to a molecule of interest, either by hydrogenation[14,15,16,17], or through reversible chemical exchange[18, 19]. By flowing molecular hydrogen through an iron oxide catalyst at sufficiently low temperature, it is possible to realize nearly 100% conversion of orthohydrogen to parahydrogen. This results in significant signal enhancements compared to that obtained using thermal polarization, which is typically in the range of $10^{-5}$-$10^{-6}$. Before proceeding, it is worth noting that light induced drift can also be used for enrichment of nuclear spin isomers in other molecules[20, 21], although the demonstrated enrichments are significantly lower, on the order of 2%. When combined with sensitive atomic magnetometers for detection of nuclear spin magnetization, PHIP enables NMR without any magnets. The sensitivity is sufficient to easily observe complex spectra exhibiting $^{1}H$—$^{13}C$ J-couplings in compounds with $^{13}C$ in natural abundance in just a few transients, a task that would require considerable signal averaging using thermal prepolarization.

To the best of our knowledge, the present invention allows for the direct observation of PHIP in a zero-field environment. The present invention shows that polarization can be transferred through a number of chemical bonds to remote parts of a molecule, and that zero-field spectroscopy can be used to distinguish between different isotopomers in ethylbenzene, the product of hydrogenation of styrene. The mechanism by which observable magnetization is generated from the parahydrogen derived singlet order requires only the presence of a heteronucleus, similar to the work of Aime[22], in contrast to a more commonly observed mechanism relevant to high field, which requires chemical-shift differences at the sites of the parahydrogen derived protons. Furthermore, the present invention could be of particular interest in the context of recent work demonstrating that the lifetime of singlet polarization in low fields can considerably exceed the relaxation time $T_1$ of longitudinal magnetization[23, 24]. These demonstrations of increased singlet lifetime relied on field cycling and high field inductive detection, and our methodology may provide for more direct observation and exploitation of these effects.

Zero-Field NMR

Zero-field NMR spectroscopy of samples magnetized by thermal prepolarization in a permanent magnet was discussed in Mcdermott[4] and Zax[25]. In an isotropic liquid at zero magnetic field, the only terms in the NMR Hamiltonian are the spin-spin J-couplings, $H_J = \Sigma \hbar J_{jk} I_j \cdot I_k$. In the important case of $AX_N$ systems, where both A and X are spin-½ particles, and each X spin couples to A with the same strength J, the resulting zero field J-spectra are simple and straightforward to interpret, consisting of a single line at J for AX, a single line at 3J/2 for $AX_2$, and two lines, one at J and one at 2J for $AX_3$. For larger molecules, as employed in the present work, long-range couplings to additional spins lead to splitting of these lines, however, the overall positions of the resulting multiplets remain unchanged. Presently we rely on numerical spin simulations (presented in detail in the Supplementary Information) to understand the splitting pattern, however we anticipate that an approach based on perturbation theory will likely yield simple rules for interpretation of the zero field splitting pattern.

Zero-field spectroscopy using parahydrogen induced polarization differs from the case of thermal polarization in both the initial density matrix and in the method of excitation. In the case of homogeneous catalysis, the product molecule starts out with two parahydrogen derived spins in a singlet state. Averaging over random hydrogenation events and subsequent evolution under the J-coupling Hamiltonian lead to an equilibrium density matrix described by pairs of heteronuclear and homonuclear scalar spin pairs, $\rho_0 = \Sigma \alpha_{jk} I_j \cdot I_k$, which bears no magnetic moment, and is static under the J-coupling Hamiltonian. Observable magnetization oscillating along the z direction, to which the magnetometer is sensitive, can be produced by applying a pulse of DC magnetic field B in the z direction. Immediately following such a pulse, the density matrix contains terms of the form $\sin\eta(I_{jx}I_{ky}-I_{jy}I_{kx})$, where $\eta=Bt_p(\gamma_j-\gamma_k)$, $t_p$ is the pulse duration, and $\gamma_j$ is the gyromagnetic ratio of spin j. Subsequent evolution under the J-coupling Hamiltonian results in terms in the density matrix of the form $(I_{jz}-I_{kz})\sin\eta\sin(J_{jk}t)$, which produces magnetization oscillating in the z direction. The dependence on $\eta$ highlights the role of a heteronucleus in the symmetry breaking of the parahydrogen derived scalar order. Numerical spin simulations of the propagation of the parahydrogen derived scalar order through the molecule and the dependence of the coherence amplitude on pulse area $\eta$ for a heteronuclear spin pair with scalar order are presented in the Supplementary Information.

Spectroscopy with Zero-Field PHIP

The zero-field spectrometer used in this work is similar to that of McDermott[4] and is shown in FIG. 7(a). The noise spectrum of the magnetometer is shown in FIG. 7(b), and the pulse sequence is shown in FIG. 7(c). Zero-field PHIP spectroscopy was performed with the present invention in hydrogenation reactions of styrene (which forms ethylbenzene) and 3-hexyne (hexene and hexane), 1-phenyl-1propyne (1-phenyl-1propene) and dimethylacetylenedicarboxlyate (dimethylmaleate). Parahydrogen was bubbled through the solution for ~10 s, the flow was halted, and excitation pulses of DC magnetic field were applied in the z direction with $\eta=\pi/2$ for $^{13}C$ and protons. The resulting z magnetization was recorded by the atomic magnetometer. The rate of hydrogenation can be monitored by the signal amplitude as a function of time.

Figure 7:
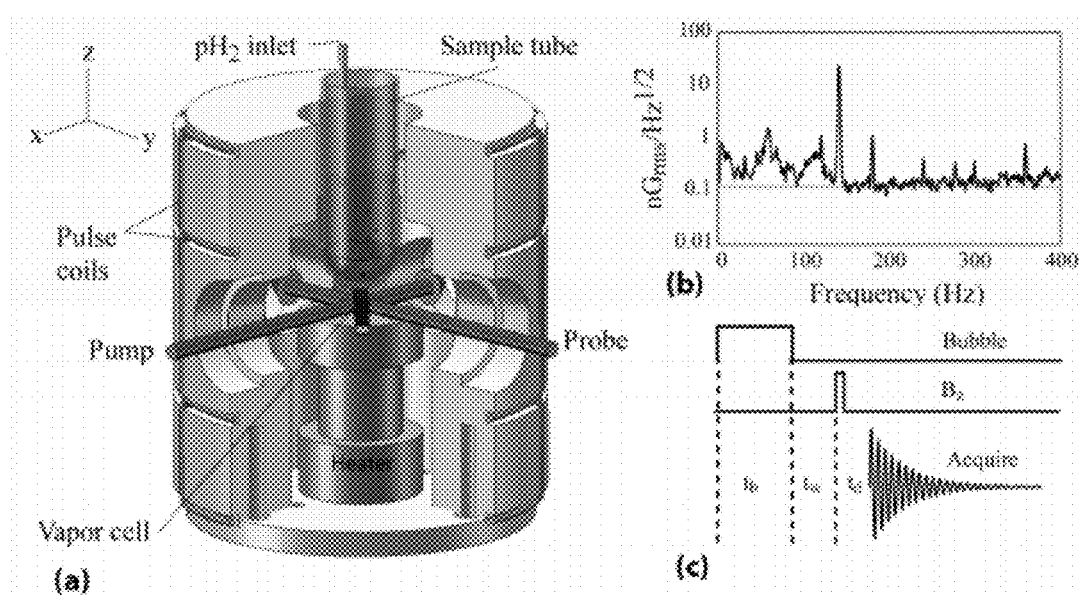
FIG. 7 shows a scheme for detecting parahydrogen induced polarization at zero magnetic-field in accordance with an exemplary embodiment of the present invention.

FIG. 7 shows a scheme for detecting parahydrogen induced polarization at zero magnetic-field in accordance with an exemplary embodiment of the present invention. The experimental setup is shown in FIG. 7(a), including a microfabricated alkali vapor cell mounted inside a set of coils used for applying magnetic field pulses. The alkali vapour is optically pumped with a circularly polarized laser beam, resonant with the D1 transition of $^{87}Rb$. A linearly polarized laser beam, tuned about 100 GHz off resonance, is used to probe the alkali spin-precession. The magnetometer is primarily sensitive to magnetic fields in the vertical (z) direction. A 7 mm inner-diameter glass tube contains the sample, and a 1/32" inner-diameter teflon tube is used to bubble parahydrogen through the solution. A set of magnetic shields surrounding the magnetometer, not shown, isolates the magnetometer from external magnetic fields. The magnetic field noise spectrum of the magnetometer is shown in FIG. 7(b). Above 100 Hz, the noise floor is about 0.15 nG/Hz$^{1/2}$. The experimental pulse sequence is shown in FIG. 7(c).

Figure 8:
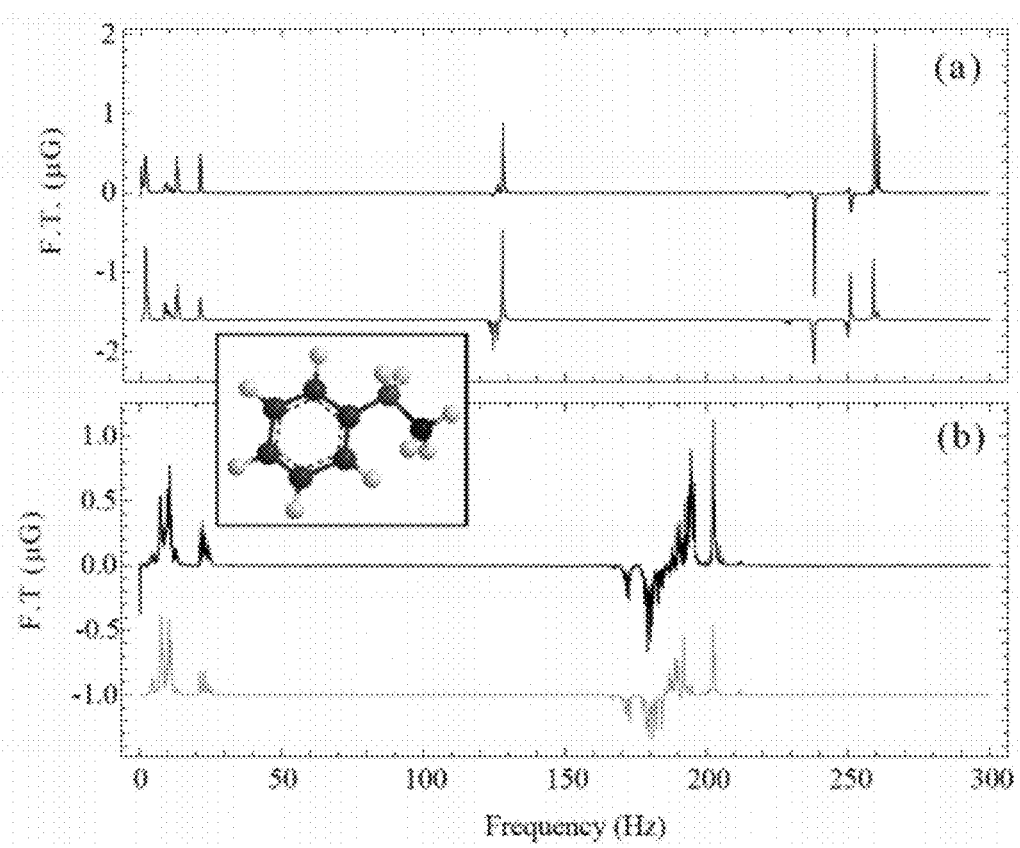
FIG. 8 shows a single-shot zero-field PHIP J-spectra (imaginary component) of ethylbenzene-$\beta^{13}$C (a) and ethylbenzene-$\alpha^{13}$C (b), polarized via addition of parahydrogen to labelled styrene, as obtained via the present invention.

Single shot, zero-field PHIP spectra of ethylbenzene-$\beta^{13}C$ (labelled $^{13}CH_3$ group), and ethylbenzene-$\alpha^{13}C$ (labelled $^{13}CH_2$ group), synthesized from labelled styrene, as obtained via the present invention, are shown in black in FIG. 8 (a) and (b), respectively. The ethylbenzene molecule is shown in the inset, with the blue carbon indicating the $\beta$ label, and the green carbon indicating the $\alpha$ label. The spectrum of ethylbenzene-$\beta^{13}C$ in FIG. 8(a) can be understood in terms of the discussion above, with multiplets at $^1J_{HC}$, and $2\times^1J_{HC}$, and additional lines at low frequency. Here the superscript indicates the number of bonds separating the interacting pair, and for ethylbenzene-$\beta^{13}C$, $^1J_{HC}=126.2$ Hz[26]. Isolated lines in the complex spectrum fit to complex Lorentzians with half-width-at-half-maximum (HWHM) of about 0.1 Hz. It should be noted that this spectrum is similar to the correspondingly labelled ethanol-$\beta^{13}C$ spectrum reported in McDermott[4], although careful inspection reveals small splittings of some lines due to long-range (at least four-bond) homonuclear couplings to protons on the benzene ring. The blue trace shows the result of a numerical simulation accounting for eight spins, including the six spins on the ethyl part of the molecule and the two nearest protons on the benzene ring.

The simulation reproduces most of the features of the experimental spectrum quite well, including small splittings of several lines.

The zero-field PHIP spectrum of ethylbenzene-$\alpha^{13}C$ shown in FIG. 8 (b) is qualitatively similar to the zero-field spectrum of ethanol-$\alpha^{13}C$ [4], with a multiplet at roughly $3/2\times^1J_{HC}$ ($^1J_{HC}=126.2$ Hz, measured in house with a 300 MHz spectrometer) and features at low frequency. Many additional lines in the spectrum indicate that long-range couplings to the protons on the benzene ring are important. Since the ethanol-$\beta^{13}C$ spectrum does not display such complexity, the largest perturbation to the ethyl part of the molecule must be due to three-bond $^3J_{HC}$ couplings. The green trace shows the result of numerical simulation, consisting of the six spins on the ethyl part of the molecule and the two nearest protons on the benzene ring. Simulation again reproduces most of features of the experimental spectrum, although careful inspection shows a number of additional splittings in the experimental spectrum, indicating that couplings to more remote spins on the benzene ring not included in the simulation, are important. It is worth emphasizing that, despite the similarity of the one-bond heteronuclear J-couplings, the spectra associated with different isotopomers display strikingly different features, which appear in different parts of the spectrum, facilitating easy assignment of isotopomers to their respective peaks.

FIG. 8 shows a single-shot zero-field PHIP J-spectra (imaginary component) of ethylbenzene-$\beta^{13}C$ (a) and ethylbenzene-$\alpha^{13}C$ (b), polarized via addition of parahydrogen to labelled styrene, as obtained via the present invention. The inset shows the ethylbenzene molecule with the $\beta$ and $\alpha$ positions indicated by the blue and green carbons, respectively. The blue and green traces in FIG. 8(a) and FIG. 8(b), respectively, are the results of numerical simulations.

Figure 9:
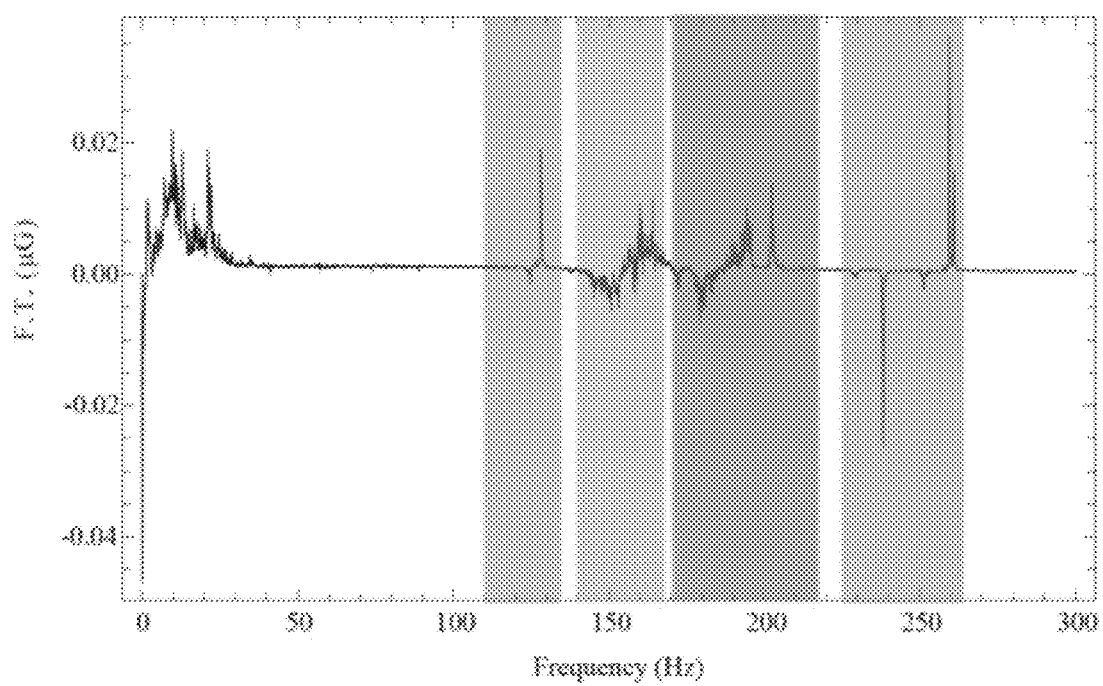
FIG. 9 shows a zero-field J-spectrum (imaginary component) of ethylbenzene, produced via parahydrogenation of styrene with $^{13}$C in natural abundance, as obtained via the present invention.

The sensitivity of the magnetometer and the degree of parahydrogen induced polarization are sufficient to detect J-spectra in compounds with $^{13}C$ in natural abundance, in accordance with an exemplary embodiment of the present invention. FIG. 9 shows the zero-field PHIP spectrum of ethylbenzene with $^{13}C$ in natural abundance, obtained in just eight transients via the present invention. The spectrum shown in FIG. 9 is the sum of spectra associated with the $\alpha$ and $\beta$ isotopomers shown in FIG. 8, as well as isotopomers that carry $^{13}C$ in one of four non-equivalent positions on the benzene ring. The high frequency parts of the spectrum arising from the $\alpha$ and $\beta$ isotopomers are highlighted in green and blue, respectively. The part of the signal arising from the benzene ring with a single $^{13}C$ is a multiplet centred about the one-bond coupling frequencies (typically about 156 Hz in aromatic systems), and also a multiplet in the low-frequency range. The high-frequency component is highlighted in red. Interestingly, spectra associated with the $\alpha$ or $\beta$ isotopomers do not overlap with spectra associated with isotopomers with a $^{13}C$ on the benzene ring. It is also noteworthy that if the hydrogenation is performed in high field, large chemical shift differences between protons on the benzene ring and the parahydrogen derived protons would inhibit the transfer of polarization to the benzene ring.

FIG. 9 shows a zero-field J-spectrum (imaginary component) of ethylbenzene, produced via parahydrogenation of styrene with $^{13}C$ in natural abundance, as obtained via the present invention. These data result from averaging 8 transients following a pulse of magnetic field in the z direction with $\eta\approx\pi/2$. The high frequency components of the signals arising from the $\alpha$ and $\beta$ isotopomers are easily recognizable from the spectra shown in FIG. 8, and are highlighted by the green and blue bands, respectively. The signal in the neighborhood of 156 Hz is due to isotopomers with $^{13}C$ on the benzene ring, and is highlighted in red.

Figure 10:
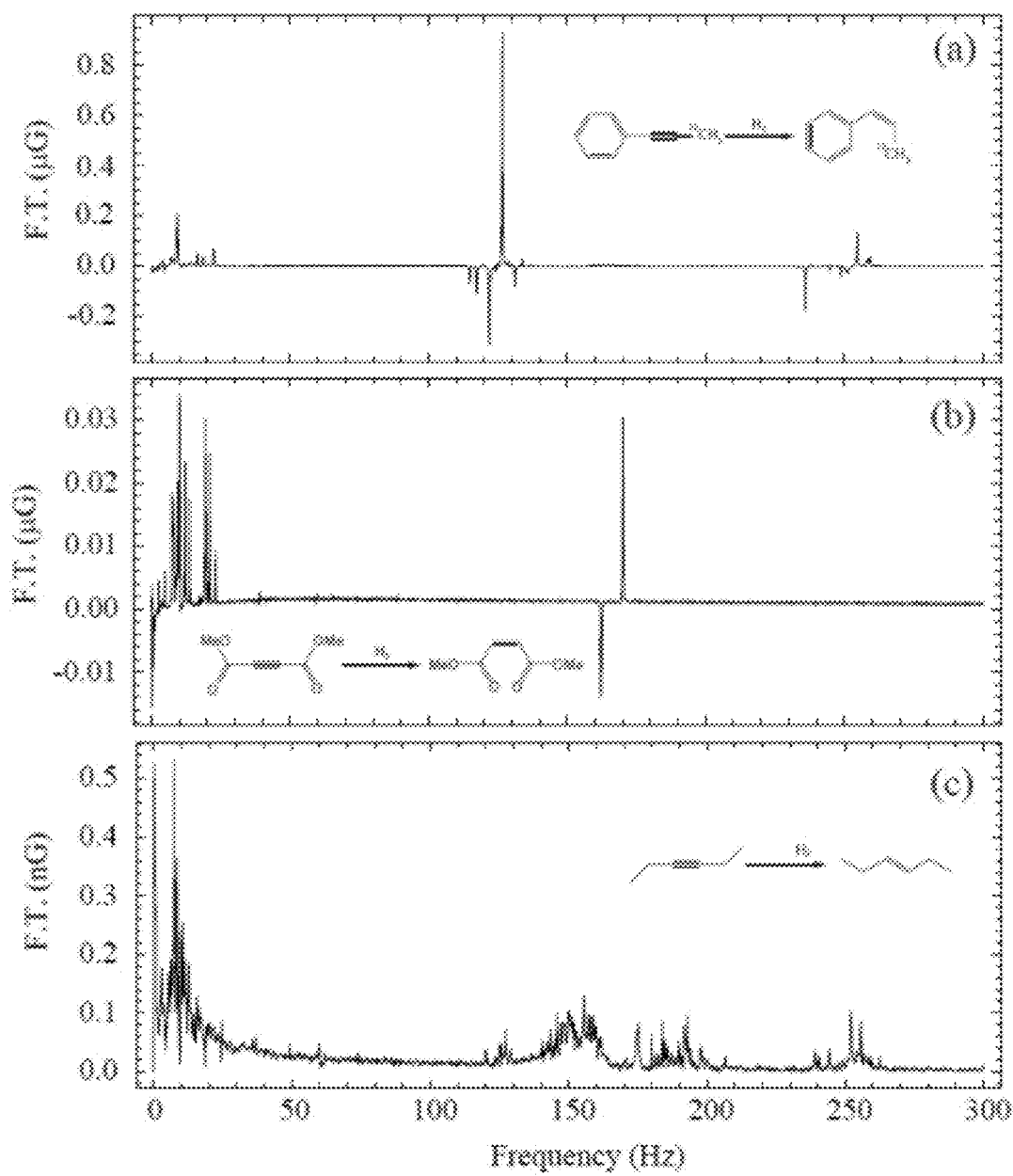
FIG. 10 shows a zero-field PHIP spectra for several compounds in accordance with an exemplary embodiment of the present invention.
Figure 11:
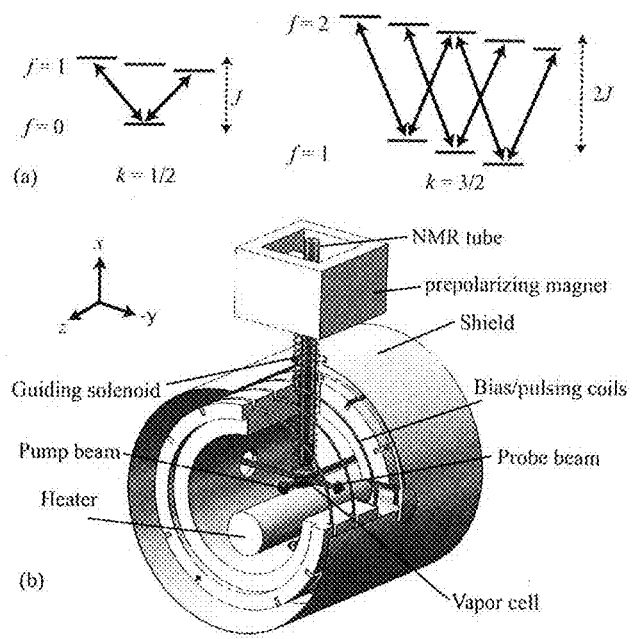
Figure 12:
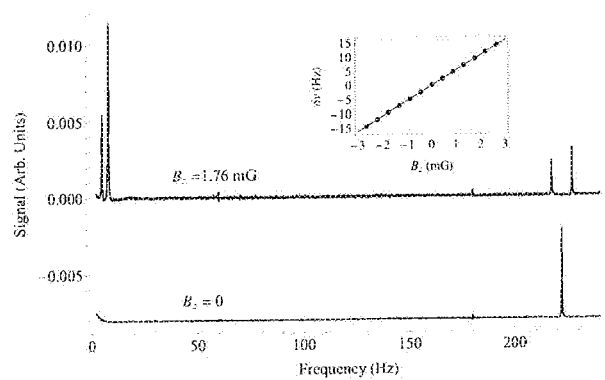
Figure 13:
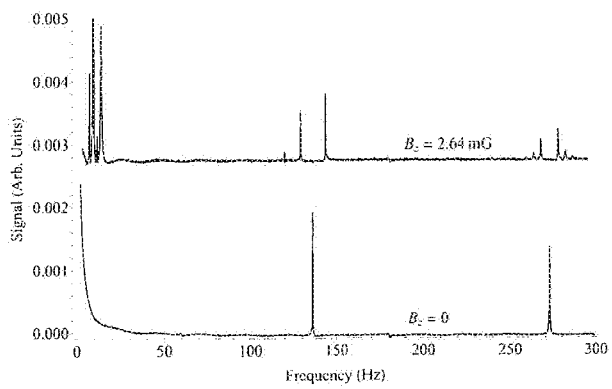
Figure 14:
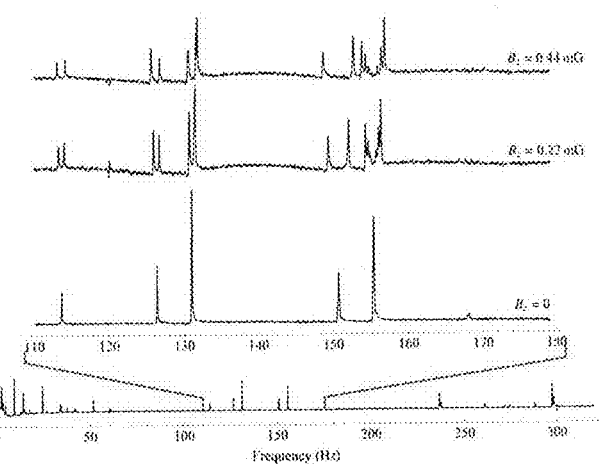
Figure 15:
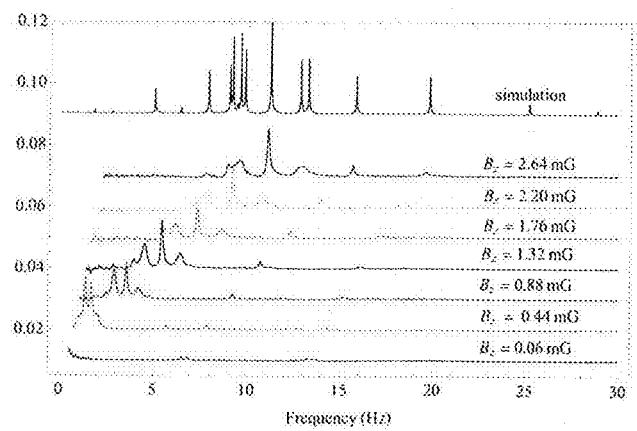

To further illustrate the capabilities of zero-field PHIP as a method for chemical fingerprinting in accordance with an exemplary embodiment of the present invention, spectra obtained from several different hydrogenation reactions are presented in FIG. 10(a) phenyl propyne (forming phenyl propene upon hydrogenation) with a labelled $^{13}CH_3$ group, FIG. 10(b) dimethyl acetylenedicarboxylate (dimethyl maleate) with $^{13}C$ in natural abundance, and FIG. 10(c) 3-hexyne (hexene and hexane) with $^{13}C$ in natural abundance. These spectra in FIG. 10 are the result of averaging 1, 6, and 32 transients respectively. The phenyl propene spectrum displays characteristics similar to the ethylbenzene-$\beta^{13}C$ spectrum, although the phase and splitting pattern is clearly different since neither of the parahydrogen derived protons are part of the labelled group. The dimethyl maleate spectrum shown in FIG. 10(b) is the superposition of two different $^{13}C$ isotopomers, and can approximately be understood as follows: For a three-spin system, where one of the parahydrogen derived spins has a strong coupling to a $^{13}C$ nucleus, one can show that the spectrum consists of two lines centred around the strong coupling frequency, and an additional low frequency peak.

The antiphase lines centred about 165 Hz in FIG. 10(b) correspond to the isotopomer where the $^{13}C$ is directly bonded to one of the parahydrogen derived spins, and is accompanied by a contribution at low frequency. The other three-spin isotopomer, where the strongest coupling to the $^{13}C$ nucleus is through two bonds, nominally gives rise to three lines at low frequency. There are some residual splittings in the low-frequency part of the spectrum, which will be the subject of future investigation. The spectrum obtained in the hexyne reaction in FIG. 10(c) is the sum of three different $^{13}C$ isotopomers. For labelled $^{13}CH_3$ groups, signal arises at $^1J_{HC}$ and $2 \times ^1J_{HC}$, where $^1J_{HC} \approx 125$ Hz. For labelled $^{13}CH_2$ groups, the contribution to the signal is centred about 3 J/2, producing signal in the range of 170 to 200 Hz. Long range couplings to other spins yield additional splitting.

FIG. 10 shows a zero-field PHIP spectra for several compounds in accordance with an exemplary embodiment of the present invention. In FIG. 10(a) parahydrogen is added to 1-phenyl-1-propyne, labelled with $^{13}C$ in the $CH_3$ group. In FIG. 10(b), parahydrogen is added to acetylene dimethylcarboxylate with $^{13}C$ in natural abundance. In FIG. 10(c) parahydrogen is added to 3-hexyne with $^{13}C$ in natural abundance FIG. 10(c). In FIG. 10(a) and FIG. 10(b), the imaginary component is presented; in (c), magnitude is presented.

Observations

The present invention can operate in zero magnetic field. Working in small but finite fields on the order of 1 mG may yield additional information regarding molecular structure, albeit at the expense of additional spectral complexity.[27]

A common objection to low- and zero-field NMR is that spectra become complex as the number of spins increase, as exemplified by comparison of the ethanol-$\alpha^{13}C$ spectrum reported in McDermott[4] and the ethylbenzene-$\alpha^{13}C$ obtained vai the present invention. The increasing complexity of spectra with spin system size is a feature that is also encountered in standard high-field NMR, and has been successfully addressed by application of multi-pulse sequences and multidimensional spectroscopy. The theory of multiple pulse sequences for zero-field NMR has been worked out some time ago[28], and presumably, many of the techniques developed for high field could be adapted to zero-field.

The present invention achieved linewidths of about 0.1 Hz. For $^{13}C$—H J-coupled systems, the dispersion in signal is about 300 Hz, so roughly 1500 lines can fit in a spectrum without overlapping. This is similar to what may be achieved in a 400 MHz spectrometer if proton chemical shifts ranging over 6 ppm and proton linewidths of about 0.5 Hz are assumed.

The sensitivity of the magnetometer used in the present invention was about 0.15 $nG/Hz^{1/2}$ using a vapour cell with a volume of 10 $mm^3$. Sensitivities about 2 orders of magnitude better have been achieved in larger vapour cells[29], which will enable measurements on larger samples with much lower concentration.

The present invention provides NMR without the use of any magnets by using parahydrogen induced polarization and a high sensitivity atomic magnetometer with a microfabricated vapour cell. The mechanism by which the symmetry of the singlet states is broken in zero field relies only upon the presence of heteronuclear J-coupling and not chemical shifts, in contrast to many experiments performed in high field. Hydrogen-carbon J-couplings through at least three bonds, and hydrogen-hydrogen couplings through four bonds are observed. It has been observed that polarization is naturally transferred through several bonds to remote parts of the molecule. This can be contrasted with in-situ hydrogenation in high field, where chemical shifts larger than J-couplings prevent efficient polarization transfer without the use of auxiliary RF pulses. Sensitivity is sufficient to perform J-spectroscopy on samples with $^{13}C$ in natural abundance with very little signal averaging. The resulting spectra, while exhibiting a large number of lines, can easily be divided into different parts, which can directly be assigned to different isotopomers of the molecule at hand. While the present invention may appear limited to molecules to which hydrogen can be added, recent advances using iridium complex catalysts enable polarization of molecules without hydrogenation[18,19], significantly expanding the scope of applicability of zero-field PHIP. Since the development of zero-field NMR is still at an early stage it is not possible to fully gauge its competitiveness with high field NMR or portable lower resolution versions thereof, but it clearly has potential to become a low cost, portable method for chemical analysis.

EXAMPLE

The invention will be described in greater detail by way of a specific example. The following example is offered for illustrative purposes, and is intended neither to limit nor define the invention in any manner.

Experimental Setup

The zero-field spectrometer of the present invention is similar to that of McDermott[4] and is shown schematically in FIG. 7 (a), including an atomic magnetometer, consisting of a Rb vapour cell and two lasers for optical pumping and probing, operates in the spin-exchange relaxation-free[8] regime. The cell is placed inside a set of magnetic shields (not shown), and residual magnetic fields are zeroed to within ≈1 µG. The vapour cell has dimensions 5 mm☐2 mm☐1 mm, contains $^{87}Rb$ and 1300 torr of $N_2$ buffer gas mm, and was microfabricated using lithographic patterning and etching techniques.

The cell is heated to 210° C. via an electric heating element wound around an aluminium-nitride spool. The sensitivity of the magnetometer is about 0.15 $nG/Hz^{1/2}$ above 120 Hz, and the bandwidth is in excess of 400 Hz. A set of coils can be used to apply sharp, ≈1 G DC pulses in arbitrary directions to excite NMR coherences, and a separate set of coils (not shown) controls the ambient magnetic field inside the shields. Mixtures of catalyst, solvent, and substrate could be brought into proximity of the atomic magnetometer via a glass sample tube.

The sample was maintained at 80° C. by flowing air through a jacket surrounding the glass tube. In experiments at lower temperature, it was found that there was some nonuniform broadening of spectra, presumably due to the presence of catalyst in solid form. Parahydrogen was bubbled through the solution via 0.8 mm inner-diameter tube for several seconds at a pressure of about 70 PSI and flow rate of about 120 standard cc/min. Bubbling was halted prior to application of excitation pulses and signal acquisition. Data were acquired with sampling rate of 2 kS/s. In acquiring the spectrum of styrene with natural-abundance $^{13}$C, the phase of the excitation pulses was cycled with respect to that of the 60 Hz line frequency in order to reduce the line noise and its harmonics.

Production of Parahydrogen

Parahydrogen was produced at 29 K by flowing hydrogen gas through a bed of iron oxide catalyst in a setup similar to that described in Koptyug[30] and then stored in an aluminium canister at room temperature and initial pressure of 150 PSI. Conversion of hydrogen to parahydrogen was about 95%, and storage lifetime was in excess of one week.

Sample Preparation

Isotopically labeled styrene was obtained from Cambridge Isotope Labs. Natural-abundance styrene and Wilkinson's catalyst[31] were obtained from Sigma-Aldrich. Styrene hydrogenations were performed with 300 μL styrene and 4 mG Wilkinson's catalyst, Tris(triphenylphosphine)rhodium(I) chloride (CAS #14694-95-2). The 1-phenyl-propyne and dimethyl acetylenedicarboxylate reactions were performed with 100 μL substrate in 300 ml tetrahydrofuran, catalyzed by 1,4-Bis(diphenylphosphino)butane](1,5-cyclooctadiene) rhodium(I)Tetrafluoroborate, (CAS #79255-71-3). The hexyne reaction was performed in a solution of 50% tetrahydrofuran with 5 mL total and 30 mG Wilkinson's Catalyst. Most of this volume does not contribute to signal since it is far from the magnetometer.

REFERENCES

1. Ernst, R. R., Bodenhausen, G., A. Wokaun, *Principles of Nuclear Magnetic Resonance in One and Two Dimensions*, Oxford University Press, New York (1987).
2. Slichter, C. P., *Principles of Magnetic Resonance*, 3$^{rd}$ ed. Springer-Verlag, New York (1990).
3. Appelt, S., Häsing, F. W., Kühn, H., Perlo, J., & Blümich, B. Mobile high resolution xenon nuclear magnetic resonance spectroscopy in the Earth's magnetic field. *Phys. Rev. Lett.* 94, 197601-197604 (2005).
4. McDermott, R. et al. Liquid-state NMR and scalar couplings in microtesla magnetic fields. *Science* 295, 2247-2249 (2002).
5. Ledbetter, M. P. et al. Optical detection of NMR J-spectra at zero magnetic field. *J. Magn. Res.* 199, 25-29, (2009).
6. Appelt, S., Kühn, H., Häsing, F. W., & Blümich, B. Chemical analysis by ultrahigh-resolution nuclear magnetic resonance in the Earths magnetic field. *Nat. Phys.* 2, 105-109, (2006).
7. Budker, D. & Romalis, M. V. Optical Magnetometry. *Nature Physics* 3, 227-234 (2007).
8. Kominis, I. K., Kornack, T. W., Allred, J. C., & Romalis, M. V. A sub-femtoTesla multichannel atomic magnetometer, *Nature*. 422, 596-599 (2003).
9. Greenberg, Y. S. Application of superconducting quantum interference devices to nuclear magnetic resonance. *Reviews of Modern Physics* 70, 175-222 (1998).
10. Ledbetter, M. P. et al. Zero-field remote detection of NMR with a microfabricated atomic magnetometer. *Proc. Nat. Acad. Sci. (USA)* 105, 2286-2290, (2008).
11. Savukov, I. M. & Romalis, M. V. NMR detection with an atomic magnetometer. *Phys. Rev. Lett.* 94, 123001/1-4 (2005).
12. Xu, S. J. et al. Magnetic resonance imaging with an optical atomic magnetometer. *Proc. Nat. Acad. Sci. (USA)* 103, 12668-12671, (2006).
13. Savukov, I. M. et al. MRI with an atomic magnetometer suitable for practical imaging applications. *J. Magn. Res.* 199, 188-191 (2009).
14. Bowers, C. R. & Weitekamp, D. P. Transformation of symmetrization order to nuclear-spin magnetization by chemical-reaction and nuclear-magnetic-resonance. *Phys. Rev. Lett.* 57, 2645-2648 (1986).
15. Natterer, J. & Bargon, J. Parahydrogen induced polarization. *Prog in Nucl. Magn. Res. Spec.* 31, 293-315 (1997).
16. Bowers, C. R. Sensitivity enhancement utilizing parahydrogen. Encyclopedia of Nuclear Magnetic Resonance 9, 750-770 Eds. D. M. Grant and R. K. Harris (2002).
17. Canet, D. et al. Para-hydrogen enrichment and hyperpolarization. *Concepts in Magnetic Resonance Part A* 28A, 321-330 (2006).
18. Adams et al. Reversible interactions with para-hydrogen enhance NMR sensitivity by polarization transfer, *Science* 323, 1708-1711 (2009).
19. Atkinson, K. D. et al., Spontaneous transfer of parahydrogen induced spin order to pyridine at low magnetic field, *J. Am. Chem. Soc.* 131, 13362-13368 (2009).
20. Chapovsky, P. L. e al. Separation and conversion of nuclear spin isomers of ethylene. *Chem. Phys. Lett.* 322, 424-428 (2000).
21. Sun, Z.-D., Takagi, K., Matsushima, F. Separation and conversion of four nuclear spin isomers of ethylene. *Science* 310, 1938-1941 (2005).
22. Aime, S., Gobetto, R., Reineri, F., Canet, D., Polarization transfer from parahydrogen to heteronuclei: The effect of H/D substitution. The case of the AA'X and $A_2A_2$'X spin systems. *J. Magn. Res.*, 178, 184-192 (2006).
23. Carravetta, M., Johannessen, O. G. & Levitt, M. H. Beyond the $T_1$ limit: singlet nuclear spin states in low magnetic fields. *Phys. Rev. Lett.* 92, 153001-153004 (2004).
24. Pileio, G., Carravetta, M. & Levitt, M. H. Extremely Low-Frequency Spectroscopy in Low-Field Nuclear Magnetic Resonance. *Phys. Rev. Lett.* 103, 083002/1-4 (2009).
25. Zax, D. B., Bielecki, A., Zilm, K. W., & Pines, A. Heteronuclear Zero-Field NMR, *Chem. Phys. Lett.* 106, 550-553 (1984).
26. Schaefer, T., Chan, W. K., Sebastian, R., Schurko, R., & Hruxka, F. E. Concerning the internal rotational barrier and the experimental and theoretical $^nJ(^{13}C, ^{13}C)$ and $^nJ(^1H, ^{13}C)$ in ethylbenzene-β$^{13}$C. *Can. J. Chem.* 72, 1972-1977 (1994).
27. Appelt, S. et al. Paths from weak to strong coupling in NMR, *Phys. Rev. A* 81, 023420/1-11 (2010).
28. Lee, C. J., Suter, D., and Pines, A., Theory of multiple-pulse NMR at low and zero fields, J. Magn. Res. 75, 110-124 (1987).
29. Dang, H. B., Maloof, A. C., & Romalis, M. V., Ultrahigh sensitivity magnetic field and magnetization measurements with an atomic magnetometer, *Apl. Phys. Lett.* 97, 151110/1-3 (2010).
30. Koptyug, I. V. et al. Para-hydrogen induced polarization in heterogeneous hydrogenation reactions. *J. Am. Chem. Soc.* 129, 5580-5586 (2007)
31. Osborn, J. A., Jardine, F. H., Young, J. F. & Wilkinson, G. The Preparation and Properties of Tris(triphenylphosphine)halogenorhodium(I) and Some Reactions Thereof Including Catalytic Homogeneous Hydrogenation of Olefins and Acetylenes and Their Derivatives. *J. Chem. Soc. A*, 1711-1732 (1966).

CONCLUSION

It is to be understood that the above description and examples are intended to be illustrative and not restrictive. Many embodiments will be apparent to those of skill in the art upon reading the above description and examples. The scope of the invention should, therefore, be determined not with reference to the above description and examples, but should instead be determined with reference to the appended claims, along with the full scope of equivalents to which such claims are entitled. The disclosures of all articles and references, including patents, patent applications, and publications, are incorporated herein by reference for all purposes.

APPENDIX

Near-zero-field nuclear magnetic resonance

We investigate nuclear magnetic resonance (NMR) in near-zero-field, where the Zeeman interaction can be treated as a perturbation to the electron mediated scalar interaction ($J$-coupling). This is in stark contrast to the high field case, where heteronuclear $J$-couplings are normally treated as a small perturbation. We show that the presence of very small magnetic fields results in splitting of the zero-field NMR lines, imparting considerable additional information to the pure zero-field spectra. Experimental results are in good agreement with first-order perturbation theory and with full numerical simulation when perturbation theory breaks down. We present simple rules for understanding the splitting patterns in near-zero-field NMR, which can be applied to molecules with non-trivial spectra.

Nuclear magnetic resonance experiments are typically performed in high magnetic fields, on the order of 10 T in order to maximize chemical shifts and to achieve high nuclear spin polarization and efficient detection via inductive pickup. The advent of various pre- or hyperpolarization schemes, and alternative methods of detection based on superconducting quantum interference devices (SQUIDs) [1] or atomic [2, 3] magnetometers has enabled NMR experiments in very low (≈earth's field) and even zero magnetic field, generating significant experimental [4–16] and theoretical interest [12, 17, 18]. Low-field NMR carries the advantage of providing high absolute field homogeneity, yielding narrow resonance lines and accurate determination of coupling parameters [9, 14]. Further, elimination of cryogenically cooled superconducting magnets facilitates the development of portable devices for chemical analysis and imaging. In this regard, atomic magnetometers are an ideal tool because, in contrast to SQUIDs, they do not require cryogenic cooling. Recent work using atomic magnetometers to detect NMR was performed at zero field, in part, because of the need to match the resonance frequencies of the nuclear spins and the magnetometer's alkali spins, which have very different gyromagnetic ratios [14, 16]. It has been pointed out that zero-field NMR leaves some ambiguity in determination of chemical groups, and that this ambiguity can be removed by application of small magnetic fields [17].

Here, we examine, experimentally and theoretically, the effects of small magnetic fields in near-zero-field (NZF) NMR. We show that application of weak magnetic fields results in splitting of the zero-field (ZF) lines, restoring information about gyromagnetic ratios that is lost in ZF NMR. In the regime where the Zeeman effect can be treated as a perturbation, we observe high-resolution spectra with easy-to-understand splitting patterns that are in good qualitative and quantitative agreement with first-order perturbation theory. This work represents the first observation of NMR under such conditions, forming the basis for a new type of NMR spectroscopy that serves as a complement to high-field NMR, where heteronuclear couplings are almost always treated as a small perturbation to the much larger Zeeman interaction. We also examine the case in which the Zeeman energies are comparable to the J-coupling energies, resulting in spectra of maximal complexity.

The Hamiltonian in the presence of J-couplings and a magnetic field is $$H = \hbar \sum_{j,k>j} J_{jk} \mathbf{I}_j \cdot \mathbf{I}_k - \hbar \sum_j \gamma_j \mathbf{I}_j \cdot \mathbf{B}. \tag{1}$$

Here $\mathbf{I}_j$ represent both like and unlike spins with gyromagnetic ratio $\gamma_j$ and $J_{jk}$ is the scalar coupling between spins $j$ and $k$. In the absence of magnetic fields, the spherical symmetry of the Hamiltonian dictates that eigenstates $|\phi_a\rangle$ are also eigenstates of $\mathbf{f}^2$ and $f_z$, where $\mathbf{f}$ is the total angular momentum $\mathbf{f} = \sum_j \mathbf{I}_j$, with energy $E_a$, and degeneracy $2f + 1$. Application of a magnetic field $B_z$ lifts this degeneracy, splitting the ZF NMR lines.

We first examine the effects of very small magnetic fields on a $^{13}CH_N$ system, with $N$ equivalent protons, using perturbation theory. In zero field, the unperturbed energy levels are given by $E(f,k) = J/2[f(f+1) - k(k+1) - s(s+1)]$, [14] where $k = 1/2, 1, 3/2...$ are the possible spin quantum numbers of the operator k describing the sum of the equivalent proton spins, and $s = 1/2$ is the spin quantum number associated with the operator s, representing the $^{13}C$ spin. To first order in $B_z$, eigenstates are those of the unperturbed Hamiltonian, and Zeeman shifts of the eigenvalues can be read from the diagonal matrix elements of the Zeeman perturbation. One finds:

$$\Delta E(f, k, m_f) = -\langle fm_f | B_z(\gamma_h k_z + \gamma_c s_z) | fm_f \rangle$$
$$= -B_z \sum_{m_k, m_s} \langle ksm_k m_s | fm_f \rangle^2 (\gamma_h m_k + \gamma_s m_s). \quad (2)$$

Here $\gamma_h$ and $\gamma_c$ are the proton and $^{13}C$ gyromagnetic ratios, and $\langle ksm_k m_s | fm \rangle$ are the Clebsch-Gordan coefficients. The observable in our experiment is the total x magnetization, $M_x(t) \propto \text{Tr}\rho(t) \sum_j I_{jx} \gamma_j$, where $\rho(t)$ is the time dependent density matrix. Writing $I_{jx}$ in terms of the raising and lowering operators, we obtain selection rules for observable coherences: $\Delta f = 0, \pm 1$ and $\Delta m_f = \pm 1$, valid in the limit where $|\gamma_j B| \ll |J|$. In the case at hand with N equivalent protons, there is an additional selection rule, $\Delta k = 0$, since, in the absence of chemical shifts, the Hamiltonian commutes with $k^2$.

Experimentally, we examine the case of $N = 1$ and $N = 3$. In the former case, $k = 1/2$, the zero-field levels are a singlet with $f = 0$ and a triplet with $f = 1$. In the presence of a small magnetic field, the singlet level is unperturbed, while the triplet levels split, as shown by the manifolds on the left of Fig. 1(a). In the following, $\nu_{f,m_f}^{f',m_f'}$ denotes the frequency of transitions between the states $|f, m_f\rangle$ and $|f', m_f'\rangle$. Employing Eq. (2) and the selection rules, one finds a single line for transitions with $\Delta f = 0$ between states with $f = 1$, and a doublet for transitions with $\Delta f = \pm 1$ between states with $f = 1$ and $f = 0$:

$$\nu_{1,m_f}^{1,m_f \pm 1} = B_z(\gamma_h + \gamma_c)/2, \quad (3)$$

$$\nu_{0,0}^{1,\pm 1} = J \pm B_z(\gamma_h + \gamma_c)/2. \quad (4)$$

For the case of $N = 3$, $k$ is either $1/2$ or $3/2$. The $k = 1/2$ transition frequencies are given by Eq. (4). The $k = 3/2$ manifolds are shown on the right of Fig. 1(a), and coherences between $|f = 1, m_f\rangle$ and $|f = 2, m_f \pm 1\rangle$ occur at frequencies given by $$\nu_{1,m_f}^{2,m_f \pm 1} = 2J + m_f \frac{B_z}{4}(-7\gamma_h + 6\gamma_c) \pm \frac{B_z}{4}(3\gamma_h + \gamma_c). \quad (5)$$

There are two additional transitions for states with $k = 3/2$ with $\Delta f = 0$ that occur near zero frequency, $$\nu_{2,m_f}^{2,m_f \pm 1} = (3\gamma_h + \gamma_c) B_z/4; k = 3/2, \quad (6)$$

$$\nu_{1,m_f}^{1,m_f \pm 1} = (5\gamma_h - \gamma_c) B_z/4; k = 3/2. \quad (7)$$

Equations. (3)-(7) constitute a set of eleven transitions, three appearing near zero frequency, two near $J$, and six

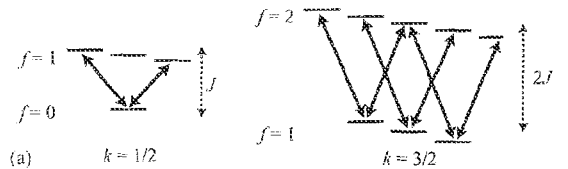

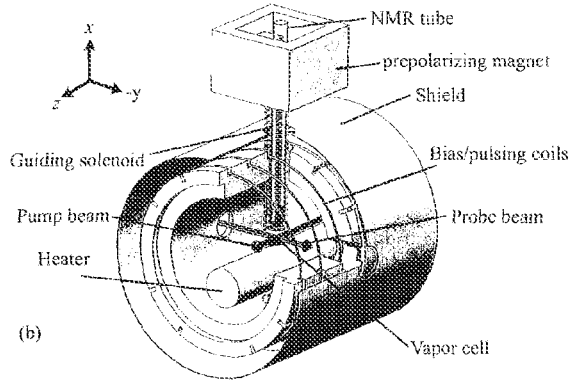

FIG. 1: (color online) (a) Energy levels for a $^{13}CH_3$ group. Energy levels for a $^{13}CH$ group are given by the manifold on the left. (b) Experimental setup for near-zero-field spectroscopy, described in the text.

near $2J$, representing the NZF NMR spectrum of a $^{13}CH_3$ group. These calculations are discussed in more depth in the Supplementary Information, and in Ref. [17].

We now make two observations: (1) Even in more complex molecules with additional non-equivalent spins, the zero-field eigenstates are also those of $f^2$ and $f_z$. Therefore, the NZF splitting patterns can be used to identify the angular momenta of the states involved in the zero-field transitions: Transitions between levels with $f = 0$ and 1 will produce doublets, transitions between levels with $f = 1$ and 2 will produce a multiplet with six lines, and so on. (2) The selection rules presented here break down as the magnetic field becomes large enough to produce significant mixing of the zero-field eigenstates. Reference [17] shows theoretically that the maximum number of lines for a $^{13}CH_N$ group is $(N+1)^2$, most clearly visible when $|(\gamma_h + \gamma_c)B_z| \approx J$.

Experiments were performed using an apparatus similar to that of Refs. [14, 16] and depicted in Fig. 1. Samples (typically $\approx 200\ \mu L$) were contained in a 5 mm NMR tube, and pneumatically shuttled between a 1.8 T prepolarizing magnet and a magnetically shielded enclosure, housing a microfabricated $^{87}Rb$ vapor cell, the central component of the atomic magnetometer. The cell is optically pumped by $z$-directed, circularly polarized laser light, tuned to the center of the D1 transition, and probed by $y$-directed, linearly polarized light, tuned about 100 GHz to the blue of the D1 transition. Optical rotation of the probe light is monitored by a balanced polarimeter. Bias fields and DC pulses of magnetic field,

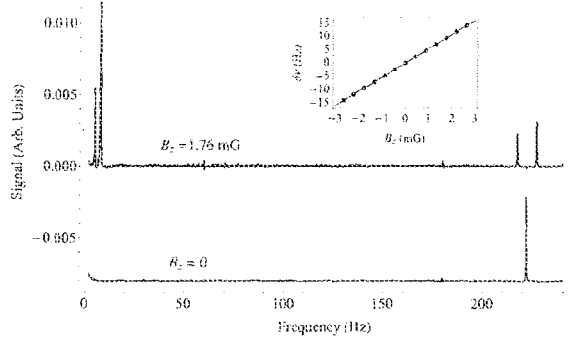

FIG. 2: Spectra for $^{13}$C labeled formic acid, H$^{13}$COOH, in the indicated magnetic fields. The spectra are the result of averaging eight transients. The inset shows the splitting of the two lines centered about $J$ as a function of magnetic field.

used to excite NMR spin coherences, are applied via a set of coils. At zero field, the magnetometer is primarily sensitive to fields in the $x$ direction with noise floor of about $40 - 50$ fT/$\sqrt{\text{Hz}}$. As the bias field is increased, the magnetometer response moves to higher frequencies, compromising the low-frequency sensitivity by about a factor of 5 for $B_z = 3$ mG. To maintain a quantization axis during transit of the sample, a solenoid provides a "guiding" field. The guiding field is turned off suddenly prior to acquisition of data, and a pulse applied in the $z$-direction with area such that the proton spins rotate through $\approx 4\pi$ and the carbon spins rotate through $\approx \pi$ (about 480 $\mu$s), maximizing the amplitude of zero-field signals.

ZF and NZF spectra for formic acid (H$^{13}$COOH) are shown in Fig. 2. The ZF spectrum consists of a single line at $J = 222$ Hz, as well as a DC component, suppressed here for clarity. The NZF spectrum arising from the $^{13}$CH group is as discussed above: a doublet with frequencies $J \pm B_z(\gamma_h + \gamma_c)/2$ and an additional line at $B_z(\gamma_h + \gamma_c)/2 \approx 4.7$ Hz. The large peak at 7.5 Hz corresponds to the uncoupled OH group. The asymmetry in the doublet centered about $J$, reproduced by a full numerical calculation, is due to higher-order corrections to the eigenstates. The peaks are well described by Lorentzians, with half-width at half-maximum $\approx 0.1$ Hz, and the locations of the peaks can be determined with an uncertainty of about 1 mHz. The inset shows the splitting of the line at $J$ as a function of magnetic field, displaying a linear dependence. The slope is in agreement with that predicted by Eq. (4), $(\gamma_h + \gamma_c)$, at the level of about 0.1%.

To illustrate the case of a $^{13}$CH$_3$ system, ZF and NZF spectra for acetonitrile-2 ($^{13}$CH$_3$CN) are shown in Fig 3. For $B_z = 0$, the spectrum consists of a zero-frequency peak, a peak at $J$, and a peak at $2J$. Application of a magnetic field splits the zero-frequency peak into three lines, whose frequencies are given by Eqs. (3),(6), and (7). The smallest peak at 11.2 Hz corresponds to an

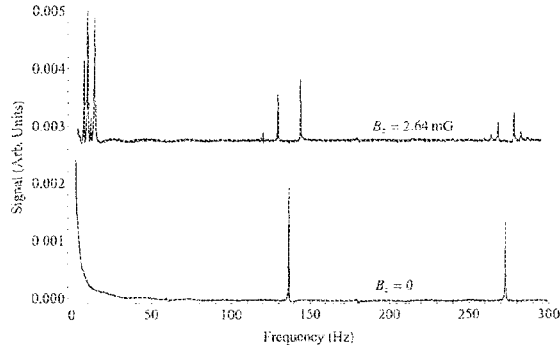

FIG. 3: Spectra for singly labeled acetonitrile-2, $^{13}CH_3CN$ in zero-field and in a field of 2.64 mG. The positions of all peaks are well described by Eqs. (3)-(7).

uncoupled proton due to an unknown solvent in the sample. The line at $J$ splits into a doublet, whose frequencies are given by Eq. (4), and the line at $2J$ splits into six lines, whose frequencies are given by Eq. (5). The splitting of the lines at $J$ and $2J$ clearly reveals the degeneracy of the zero-field levels. As with the formic acid spectrum, there is some asymmetry present in the multiplets centered about $J$ and $2J$, which is reproduced by numerical simulation. Nevertheless, the relative amplitudes of the lines centered about $2J$ are roughly in the ratio 1:3:6:6:3:1 as expected from first-order perturbation theory (see Supplementary Information).

To illustrate the utility of NZF NMR, we examine the case of fully labeled acetonitrile ($^{13}CH_3\,^{13}C^{15}N$). The zero field spectrum is shown in the bottom trace of Fig. 4. It is not immediately clear which lines correspond to which zero-field transitions. An expanded view of the zero-field spectrum in the range of 110 to 180 Hz is provided and compared to the spectrum obtained in the indicated finite magnetic fields. We see the appearance of doublets centered at 114, 126, and 151 Hz, indicating that these transitions occur between manifolds with $f = 0$ and $f = 1$. It is interesting to note that these doublets display different splittings due to differences in the Landé $g$ factors for the different manifolds involved in these transitions. The line at 131 Hz splits first into a doublet, which split into a pair of doublets. One can show that such a splitting pattern arises for a $f = 1 \leftrightarrow f = 1$ (see Supplementary Information). The small zero-field peak at 168 Hz splits into four lines, barely above the noise, indicating an additional $f = 1 \leftrightarrow f = 1$ transitions. Finally, the zero-field peak at 155.5 Hz splits into a sextet indicating the transition is $f = 1 \leftrightarrow f = 2$. The six lines in this multiplet appear "inside-out" compared to the six line multiplet observed at $2J$ in 2-acetonitrile due to a reversal in relative magnitude of the Landé $g$ factor.

The multiplicity of the peaks in this part of the spectrum can be understood as follows: Suppose we start

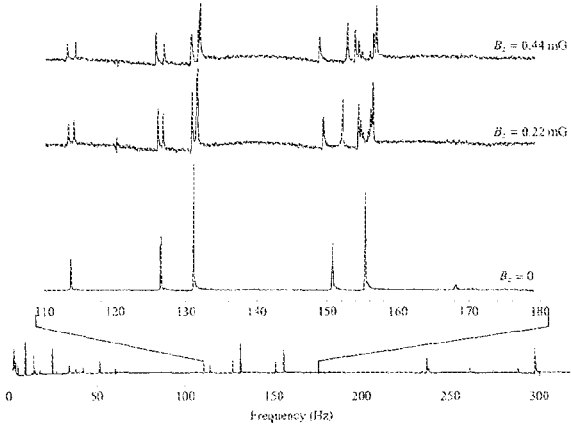

FIG. 4: Effects of small magnetic fields on fully labeled acetonitrile $^{13}CH_3^{13}C^{15}N$. The bottom trace shows the entire zero-field spectrum. The upper traces show an expanded view of the central part of the zero-field spectrum, as well as the spectra in the indicated finite fields.

with a $^{13}CH_3$ group, and confine our attention to the $1 \leftrightarrow 0$ transition with total proton spin $= 1/2$, yielding transitions in the neighborhood of $^1J_{CH}$. Addition of the second $^{13}C$ splits these levels: $f = 1$ splits to $3/2$, $1/2$ manifolds, and $f = 0$ manifolds splits to $1/2$. Addition of the $^{15}N$ splits these so we now have $f_a = 2$ or $1$, $f_b = 1$ or $0$, and $f_c = 1$ or $0$. For now, we ignore transitions between $f_a \leftrightarrow f_b$ because they occur at low frequency. Employing the $\Delta f = 1$ rule we expect three $1 \leftrightarrow 0$ transitions, producing doublets: $f_a = 1 \leftrightarrow f_c = 0$, $f_b = 1 \leftrightarrow f_c = 0$, and $f_b = 0 \leftrightarrow f_c = 1$. Transitions between $f_a = 2 \leftrightarrow f_c = 1$ yields a multiplet with six lines, and transitions with $\Delta f = 0$ between $f_a = 1 \leftrightarrow f_c = 1$ and between $f_b = 1 \leftrightarrow f_c = 1$ yield multiplets with four lines. More details are presented in the Supplementary Information.

In systems with small couplings, such as 1-acetic acid ($CH_3{}^{13}COOH$) which has a two-bond coupling, $^2J_{CH} = 6.8$ Hz, it is possible to explore the regime in which the Zeeman interaction is comparable to the $J$-coupling. Figure 5 shows experimental spectra for 1-acetic acid for the indicated magnetic fields. The large peak that does not split is due to the uncoupled OH group, while the rest of the spectrum corresponds to the $CH_3{}^{13}C$ part of the molecule. Initially, the spectrum appears similar to the 2-acetonitrile spectrum, with a doublet at $J$, and an additional doublet at $2J$ composed of several unresolved lines. As the magnetic field is increased, additional lines in the multiplet at $2J$ become resolved. At the highest magnetic fields, the spectrum displays the highest complexity, and is no longer recognizable from the perturbative treatment presented above. The smooth trace at the top of the plot shows the log of the absorptive component of a high resolution numerical simulation, reproducing all features of the data, to the extent that lines are resolved.

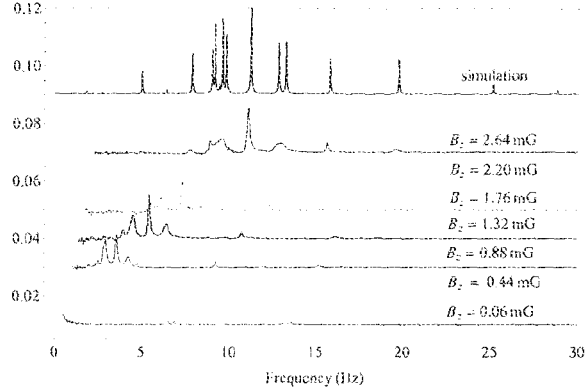

FIG. 5: Experimental spectra for 1-acetic acid, ($CH_3^{13}COOH$) in the indicated magnetic fields. The smooth curve at the top of the plot presents the result of a full numerical simulation with high resolution.

Careful examination reveals 17 lines, 1 for the OH group and $(N+1)^2 = 16$ lines, as theoretically predicted in Ref. [17].

In conclusion, we have investigated near-zero-field nuclear magnetic resonance, where the effects of magnetic fields can be treated as a perturbation to the scalar $J$-couplings. This work represents a new form of NMR spectroscopy, complementary to high-field NMR, in which heteronuclear scalar couplings are almost always treated as a small perturbation to the dominant Zeeman interaction. We find that the presence of small fields produces splitting of zero-field lines. The splitting patterns have easy-to-understand rules and data are in excellent agreement with the predictions of first-order perturbation theory. It is interesting to note that the phenomenology observed here is similar to that of atomic spectroscopy of multi-electron atoms, and intuition developed in the latter field may be applied to interpretation of NZF NMR spectra. We have also investigated the case where Zeeman and $J$-couplings are comparable, resulting in signals with much higher complexity, potentially useful for NMR quantum computing [17].

This research was supported by the National Science Foundation under award #CHE-0957655 (D. Budker and M. P. Ledbetter) and by the U.S. Department of Energy, Office of Basic Energy Sciences, Division of Materials Sciences and Engineering under Contract No. DE-AC02-05CH11231 (T. Theis, J.W. Blanchard, H. Ring, P. Ganssle and A. Pines). We thank S. Knappe and J. Kitching for supplying the microfabricated alkali vapor cell.

[1] Y. S. Greenberg, Rev. Mod. Phys. 70, 175 (1998).
[2] D. Budker, and M. Romalis, Nat. Phys. 3, 227 (2007).
[3] T. W. Kornack et al., Appl. Phys. Lett. 90, 3 (2007).
[4] R. McDermott et al., Science 295, 2247 (2002).
[5] A. H. Trabesinger et al., J. Phys. Chem. A 108, 957 (2004).
[6] S. Appelt, F.W. Häsing, H. Kühn, J. Perlo, and B. Blümich, Phys. Rev. Lett. 94, 197602/1 (2005).
[7] I. M. Savukov, and M. V. Romalis, Phys. Rev. Lett. 94, 123001/1 (2005).
[8] S. J. Xu et al., Proc. Nat. Acad. Sci. (USA) 103, 12668 (2006).
[9] S. Appelt et al., Nat. Phys. 2, 105 (2006).
[10] J. N. Robinson et al., J. Magn. Res. 182, 343 (2006).

[11] I. M. Savukov, S. J. Seltzer, and M. V. Romalis, J. Magn. Res. 185, 214 (2007).
[12] S. Appelt, F.W. Häsing, H. Kühn, and B. Blümich, Phys. Rev. A 76, 023420 (2007).
[13] M. P. Ledbetter et al., Proc. Nat. Acad. Sci. (USA) 105, 2286 (2008).
[14] M. P. Ledbetter et al., J. Magn. Res. 1999 25 (2009).
[15] S. Appelt et al., Chem. Phys. Lett. 485, 217 (2010).
[16] T. Theis et al. Nat. Phys., in press.
[17] S. Appelt et al., Phys. Rev. A 81, 023420 (2010).
[18] G. Kervern et al. manuscript in preparation.
[19] O. W. Sørensen, H. Bildsöe, and H. J. Jakobsen, J. Magn. Res. 45, 325 (1981).

What is claimed is:

1. A method of detecting a J-coupling comprising:
   (a) providing an analyte in a detector cell adjacent to a vapor cell of an atomic magnetometer, the analyte being polarized, the detector cell and the vapor cell being housed in a magnetic shield that isolates the detector cell and the vapor cell in a static magnetic field;
   (b) applying a magnetic field pulse to the analyte in the detector cell; and
   (c) detecting a magnetic field generated by the analyte using the atomic magnetometer as a magnetization of the analyte evolves under one or more J-coupling interactions.

2. The method of claim 1 further comprising:
   polarizing the analyte before operation (a).

3. The method of claim 2 wherein polarizing the analyte employs a polarization technique selected from a group consisting of thermalization in a magnetic field, spin-exchange optical pumping, para-hydrogen induced polarization, and dynamic nuclear polarization.

4. The method of claim 1 further comprising:
   transporting the analyte to the detector cell.

5. The method of claim 1 wherein the one or more J-coupling interactions are selected from a group consisting of a heteronuclear scalar coupling, a homonuclear scalar coupling, and a combination thereof.

6. The method of claim 1 further comprising:
   generating a graph of the one or more J-coupling interactions.

7. The method of claim 1 wherein a magnitude of the static magnetic field is less than about 2.5 nanotesla.

8. The method of claim 1 wherein a larmor precession frequency of the analyte is less than about 100 mHz in the static magnetic field.

9. The method of claim 1 wherein a magnitude of the static magnetic field is less than about 100 microtesla.

10. The method of claim 1 wherein the magnetic field pulse is applied by applying a pulse of DC current to coils positioned in the magnetic shield.

11. The method of claim 1 wherein a magnitude of the static magnetic field is less than about 1 millitesla.

* * * * *